United States Patent
Lohse

(10) Patent No.: US 10,718,777 B2
(45) Date of Patent: Jul. 21, 2020

(54) COMBINED HISTOLOGICAL STAIN

(75) Inventor: Jesper Lohse, Herlev (DK)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 224 days.

(21) Appl. No.: 13/991,701

(22) PCT Filed: Dec. 6, 2011

(86) PCT No.: PCT/DK2011/000148
§ 371 (c)(1),
(2), (4) Date: Aug. 29, 2013

(87) PCT Pub. No.: WO2012/076010
PCT Pub. Date: Jun. 14, 2012

(65) Prior Publication Data
US 2013/0337441 A1 Dec. 19, 2013

Related U.S. Application Data

(60) filed as application No. PCT/DK2011/000148 on Dec. 6, 2011.

(60) Provisional application No. 61/419,949.

(51) Int. Cl.
*G01N 33/58* (2006.01)
*G01N 33/86* (2006.01)
*G01N 33/52* (2006.01)
*G01N 33/53* (2006.01)

(52) U.S. Cl.
CPC .......... *G01N 33/581* (2013.01); *G01N 33/52* (2013.01); *G01N 33/53* (2013.01); *G01N 33/86* (2013.01)

(58) Field of Classification Search
CPC ...... G01N 33/581; G01N 33/52; G01N 33/53; G01N 33/86
See application file for complete search history.

(56) References Cited

U.S. PATENT DOCUMENTS

| | | |
|---|---|---|
| 2005/0054017 A1* | 3/2005 | Smeal et al. .................. 435/7.23 |
| 2005/0196844 A1* | 9/2005 | Lee .................... G01N 33/6896 435/70.21 |
| 2009/0047690 A1* | 2/2009 | Goldberg .................... 435/7.24 |

FOREIGN PATENT DOCUMENTS

| | | | |
|---|---|---|---|
| CN | 102713626 A | 10/2012 | |
| WO | WO02088376 A2 | 11/2002 | |
| WO | WO2006116628 A2 | 11/2006 | |
| WO | WO 2007130677 A2 * | 11/2007 | .......... G01N 33/50 |
| WO | 2009036760 A2 | 3/2009 | |
| WO | 2010094284 A1 | 8/2010 | |
| WO | WO2010094283 A1 | 8/2010 | |
| WO | 2011047680 A1 | 4/2011 | |

OTHER PUBLICATIONS

Van der Loos, Multiple Immunoenzyme staining: Methods and visualizations for the observation with spectral imaging, Journal of Histochemistry & Cytochemistry, 313-328, 2008.*
Yamamoto et al., Phosphorylation of tau at serine 416 by Ca2+/calmodulindependent protein kinase II in neuronal soma in brain, Journal of Neurochemistry, 2005, 94, 1438-1447.*
Ryuichi Okamoto et al., "Damaged Epithelia Regenerated by Bone Marrow-Derived Cells in the Human Gastrointestinal Tract," Nature Medicine, vol. 8, No. 9, Sep. 2002, pp. 1011-1017.
Hiroaki Nitta, et al., "Development of Automated Brightfield Double In Situ Hybridization (BDISH) Application for HER2 Gene and Chromosome 17 Centromere (CEN 17) for Breast Carcinomas and an Assay Performance Comparison to Manual Dual Color HER2 Fluorescence In Situ Hybridization (FISH)," Diagnostic Pathology. Oct. 22, 2008, BioMed Central (12 pages).
C. M. Van Der Loos: "Multiple Immunoenzyme Staining: Methods and Visualizations for the Observation With Spectral Imaging," Journal of Histochemistry & Cytochemistry, vol. 56, No. 4, Apr. 1, 2008, pp. 313-328, Sage Publications.

* cited by examiner

*Primary Examiner* — Andrea S Grossman

(57) ABSTRACT

The present invention relates to methods of visualizing targets in histological samples, e.g. biopsy samples, wherein the methods comprise staining of the sample with (i) one or more target specific immunochemical stains, and (ii) a histological stain for specific tissue components e.g. iron, mucins glycogen, amyloid, nucleic acids, etc., e.g. hematoxilyn and/or eosin stains or the like, that is used to enhance contrast in the microscopic image of a tissue sample, highlight morphologic structures in the sample for viewing, define and examine tissues, cell populations, or organelles within individual cells. Methods may further comprise evaluation of expression of one or more targets in the sample. The disclosed methods are useful for medical diagnostics.

21 Claims, 1 Drawing Sheet

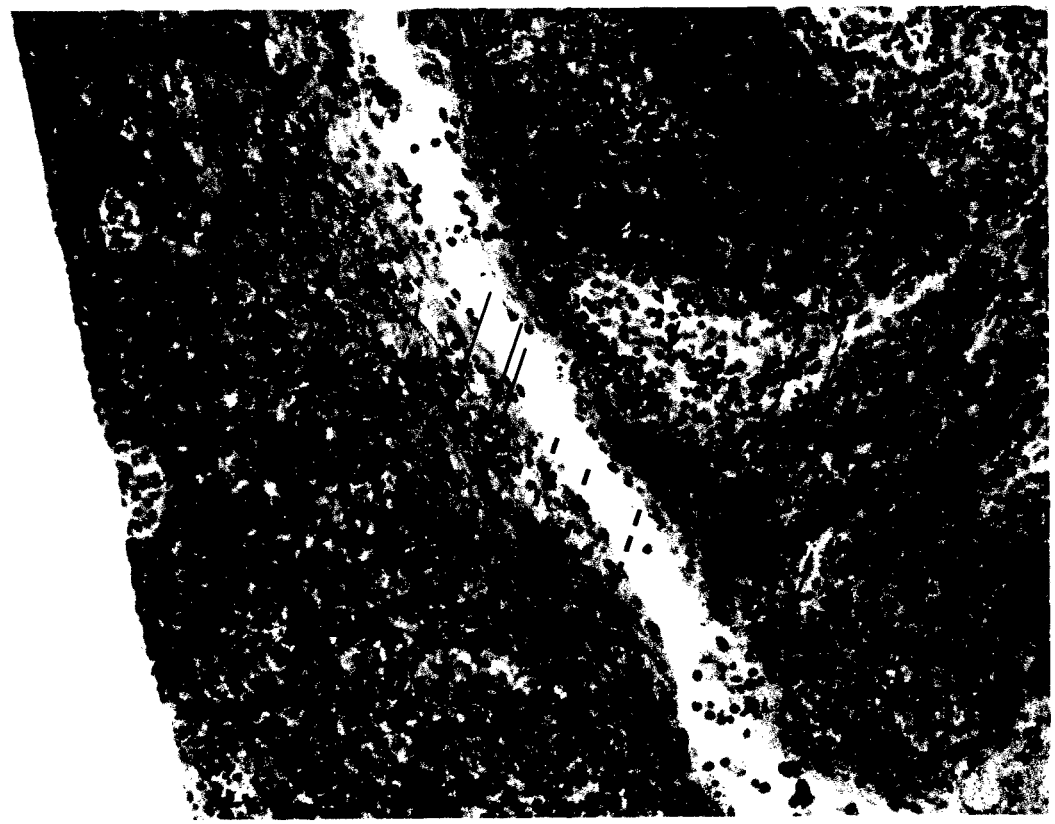
↓ Dotted pattern of Her2 stain of step (a)
↙ Conventional pattern of Her2 stain of step (b)
↙ Hematoxylin staining of nuclei of step (c)

COMBINED HISTOLOGICAL STAIN

FIELD OF INVENTION

The present invention relates to methods of visualizing targets in histological samples, e.g. biopsy samples, wherein the methods comprise staining of the sample with one or more target directed immunochemical stains, and a histological stain for specific tissue components e.g. iron, mucins glycogen, amyloid, nucleic acids, etc., e.g. hematoxilyn and/or eosin stains or the like, that is used to enhance contrast in the microscopic image of a tissue sample, highlight morphologic structures in the sample for viewing, define and examine tissues, cell populations, or organelles within individual cells.

BACKGROUND OF INVENTION

Histopathology, the microscopic study of diseased tissue, is an important tool in anatomical pathology, since accurate diagnosis of cancer and other diseases usually requires histopathological examination of samples.

Analysis of the microscopic anatomy of a sample of patient tissue is usually performed by examining under a light microscope a thin slice (section) of tissue of a patient loaded on a glass slide. The ability to visualize or differentially identify microscopic structures is frequently enhanced through the use of histological stains. Hematoxylin and eosin (H&E) stain is the most commonly used light microscopical stain in histology and histopathology, wherein hematoxylin is used to stain nuclei blue, while eosin stains cytoplasm and the extracellular connective tissue matrix pink.

In addition to H&E stain special stains can be applied to answer questions that arise beyond those that can be answered by interpreting H&E-stained tissue morphology. Some useful applications of special stains to mention are: determination of DNA and RNA content, metabolic biochemistry, biochemistry of disease processes, primary sites of many metastatic tumors, identification of non-pigmented metastatic melanomas, detection of early invading tumors, etc. (see e.g. Education Guide: Special stains and H&E, $2^{nd}$ edition, Kumar G L and Kleman G A eds, Dako, 2010).

Immunohistochemistry (IHC) has now replaced many traditional "special stains" because of IHC stains have great specificity. Most commonly used IHC stains, e.g horseradish peroxidase (HRP) or alkaline phosphotase (AP) substrate based IHC stainings, provide a special stain alike uniform staining pattern that appears to the microscopist as a homogeneous color with intracellular resolution of cellular structures, e.g. membrane, cytoplasm, and nucleus.

IHC staining is a common tool in medical diagnostics and it is also usual for the assessment of therapeutic biomarkers. However, despite of IHC stains are exceptionally precise in the recognition of specific targets or epitopes throughout the sample and allow quantification of these targets and epitopes, they are too expensive to use in routine evaluation of general morphology of a tissue sample. Therefore, H&E and special stains still remain an important tool for pathologists and technologists providing an essential complement to IHC as a diagnostic technology that defines a patient's medical profile. However, until now there has not been described any histological staining method which would allow evaluating morphological characteristics of the tissue, precise target localization and its content distribution in one and the same tissue sample obtained from a patient.

As mentioned above, a conventional IHC staining employing chromogenic and fluorescent reporters that mark targets in histological samples allows some quantification of these targets (and epitopes). However, this quantification is not precise as it employs a densitometric analysis of the signal and correlating the level of reporter signal to the level of target (e.g. protein) expression or localization. New recently developed super sensitive IHC visualization systems (see PCT/DK2010/000137 and PCT/DK2011/000131) allow now visualizing and quantifying single molecules of targets (e.g. proteins) in histological samples, but these systems have a drawback that they do not reveal and, thus, not allow analyzing tissue morphology of the samples.

Therefore, it would be of a great advantage to have a method allowing visualizing and precisely quantifying molecular targets in histological samples stained with a histological stain as it would allow accurate diagnosis and effective therapy of cancer and other diseases that require both histopathological examination of samples and quantification and quantification of biomarkers of these diseases.

DESCRIPTION OF DRAWINGS

FIG. 1 shows a representative microphotograph of a combined histological staining of a tonsil tissue sample visualizing Her2 protein (expression level 2+ according to Hercept test).

SUMMARY OF THE INVENTION

The invention provides methods for visualization of targets in histological samples, wherein the methods comprise staining of said histological samples with at least two different stains, wherein at least one of said stains is an immunochemical stain suitable for use in immunohistochemistry (further referred as immunohistochemical stain or IHC stain) to visualize sites of the sample that comprise the target (referred herein as "target sites") as distinct dots, and at least one of said stains is a histological stain that is used in microscopy to enhance contrast in the microscopic image of a tissue sample, highlight structures in the sample for viewing, define and examine bulk tissues (e.g. highlighting connective tissue), or cell populations (e.g. classifying different blood cells), or organelles within individual cells, e.g. hematoxylin stain or the like, i.e. a histological stain that is capable of visualizing morphology of a tissue sample on the microscopic level.

In one embodiment the invention relates to methods for visualization of targets in histological samples comprising staining of said histological samples with at least three different stains, wherein at least two of these stains are two IHC stains that visualize target sites in the sample, and at least one stain is a histological stain that visualizes morphology of the sample. According to the invention the at least two target sites directed IHC stains defers from each other by both sensitivity of detection of the target sites in the sample and optical appearance in the stained sample: a first of said at least two IHC stains visualizes a minor fractional sub-population of single target sites, wherein at least a portion of said target sites comprises single target units, and appears to the microscopist as distinct dots of stain marking said single target sites; a second of said at least two IHC stains visualizes the bulk of the target sites in the sample and appears to the microscopist as a homogeneous color (I.e. without apparent resolution into distinct dots marking single target sites).

the method provides a uniform staining pattern that appears to the microscopist as a homogeneous color with intracellular resolution of cellular structures, e.g. membrane, cytoplasm, and nucleus, which makes it impossible to quantify the staining accurately.

In particular, in one embodiment, the invention relates to a method of method for visualization of a target in a histological sample, comprising in any order
(a) staining the sample with a first stain,
(b) staining the sample with a second stain,
(c) staining the sample with a third stain,
wherein
(i) the first stain and the second stain are generated via an enzyme mediated deposition of a detectable enzyme substrate at sites of the sample comprising units of the target;
(ii) the first stain visualizes a first fractional sub-population of target units, and the second stain visualizes a second fractional sub-population of target units;
(iii) the first stain and second stain have different staining patterns,
wherein the first stain staining pattern consists of distinct dots of the stain at sites of the sample comprising target units;
and
(iv) the third stain is a histological stain that visualize morphological features of the tissue sample and does not visualize the target.

In another embodiment, the invention relates to a method for visualization of two or more targets in a histological sample, comprising in any order
a. staining the sample with a first stain,
b. staining the sample with a second stain,
c. staining the sample with a third stain,
wherein
(i) the first stain and the second stain are generated via an enzyme mediated deposition of a detectable enzyme substrate at sites of the sample comprising the target;
(ii) the first stain visualizes target sites comprising units of a first target;
(iii) the second stain visualizes target sites comprising units of a second target;
(iv) the first stain and second stain are distinguishable by their staining patterns, wherein the staining pattern of the first stain is characterized in that it consists of distinct dots, and the staining pattern of the second stain is a uniform staining pattern of homogenous color; and
(v) the third stain is a histological stain that visualize morphological features of the tissue sample and does not visualize the target Advantageous features of the methods of the invention allow simultaneously visualizing the bulk of the target and single target entities (the same or different targets) of such as targets as proteins or cytoplasmic nucleic acids in one and the same histological sample stained with a histological stain. Use of a histological stain advantageously reveals characteristic morphological appearance of tissue of the sample for microscopic evaluation of the regional expression of the target(s) in the sample. Use of affinity binding agents for detection the target and powerful signal amplification systems allowing detect single target molecules (or other single target entities) makes the methods of the invention an indispensible tool for a precise quantification of targets in histological samples, in particular for medical diagnostics based on evaluation of biological samples comprising cells, e.g. for cancer diagnostics.

DETAILED DESCRIPTION OF THE INVENTION

The invention generally relates to methods of visualization and quantification of targets of interest, in particular molecular targets, in histological samples, wherein the morphology of samples is visualized by staining of the samples with a histological stain, and wherein the targets are detected by use of target specific binding agents and sites of the sample comprising the target are visualized by use of enzyme-mediated depositions of detectable enzyme substrates at sites of the sample—

DEFINITIONS AND EMBODIMENTS

1. Histological Sample

The invention generally relates to histological samples or the like. The term "sample" means a representative part of a larger whole or group, an amount or portion of a matter or object that may or may not contain a target to be detected. The term "histological sample" means that the sample contains biological material comprising cells and/or cell debris, e.g. a body tissue sample, a sample of a cell culture, e.g. cloned cells, a sample body tissue homogenate, etc; a sample comprising of intact or damaged cells of an animal body, a body tissue, smear or fluid or a sample of a tumor, e.g. a biopsy sample; a sample comprising a living organism, e.g. a sample of a medium comprising an animal, plant, bacterium, fungi, etc; a sample comprising viral particles, debris thereof, or viral products, e.g., a body smear comprising viral nucleic acids, proteins, peptides, etc; a sample comprising a cell organelle(s); a sample comprising natural or recombinant biological molecules, e.g. blood plasma sample, conditioned cell culture media, etc.; a sample comprising plant cells or derbies thereof.

A histological sample may be a sample a fresh body or tumor tissue sample. In one embodiment a histological sample may be a sample of a pseudo tissue. The term "pseudo tissue" in the present content means an artificial matter that comprises cells and/or cell debris embedded into a media and, optionally, one or more other components that compose a natural biological tissue, and which under microscopic observation morphologically reminds a sample of a body tissue or tumor sample.

The above mentioned examples of histological samples are not limiting.

2. Target

In one embodiment the methods of the invention may relate to a histological sample that comprises a target (which is to be visualized), e.g. a protein that is a biomarker of a disease, in another embodiment a histological sample may not comprise the target, e.g. a control histological sample, in another embodiment, the invention may relate to a histological sample that supposedly comprise the target, e.g. a sample of a tissue which may, or may not, contain a target protein.

The term "target" means in the present content an object of interest supposedly present in a sample that can be characterized by particular physical and/or functional features. It is understood that in the context of the invention the term "target" relates to the whole pool of substantially identical entities of that object, not to a single entity of that object in a sample; in samples where a target is represented by the only single unit, this only single target unit is to be understood as the target at whole. The term "substantially identical" in the present context means that all or substantially all single entities of the total pool of a target in a sample possess one or more features that make them recognizable as the target. For example, the target may be a particular protein (including all individual molecules of that particular protein in the sample), a molecular aggregate, molecular complex or structure, virus or bacterium, wherein all individual molecules of that particular protein, all molecular aggregates, molecular complexes, structures, viral particles or bacteria in the sample are referred as the target, and their individual entities as single target units.

Some biological molecules, molecular complexes, structures, particles or organisms are associated with features that are considered to be characteristic for particular cell types, tissues, cellular structures, physiological conditions, etc. and are often referred as "biological markers" of these particular cell types, tissues, cellular structures, or physiological conditions. In one embodiment the invention relates to a target which is a biological marker.

In one embodiment, the target may be a protein, e.g. a cellular membrane receptor or a cytoplasmic protein, in another embodiment the target may be a nucleic acid, e.g. a cytoplasmic nucleic acid. Derivatives of any latter mentioned targets, e.g. fragments, precursors, mutants of target proteins or nucleic acids, etc. may also be targets in some embodiments of the invention.

Thus, in different embodiments of the invention the target may be a biological or chemical target molecule, or a particle, or a molecular or cellular complex, or molecular or cellular structure, or a virus, or a microorganism, or a fragment of said target molecule, particle, complex, structure, virus or microorganism. Among targets detectable by the methods of the invention contained in histological samples may be different pollutants, toxins, warfare substances, members of molecular libraries, etc.

In one embodiment the invention relates to a target which is presented in a sample as a plurality of single substantially identical units.

By the term "unit" is meant a quantity of a target which is separable from the other quantities of the target or from other components of the environment by physical features and/or a function and can be considered and counted separately. The term "individual target unit" or "single target unit" in the present content means that a target unit is one in number as opposed to or in contrast with many. For example a single/individual unit of a target protein means a single individual protein molecule of the target protein, i.e. one molecule of plurality of molecules the same kind. The term "substantially identical units" means that a plurality of single units of a target possesses one or more features that make these units be considered as the target. The term "independent" means that a single unit of a target exists as a distinct entity and do not depend on the existence of other distinct entities of the same kind in the sample.

The invention some embodiments relates to a single target unit which is part of a target molecule, structure, aggregate or complex that has some properties that allow distinguishing this part of the molecule from the other parts of the same molecule, structure, aggregate or complex. Non-limiting examples of these embodiments may be functional domains of protein molecules, epitopes, proteolytic fragments of target proteins, parts of fusion molecules, particular structures of nucleic acids, etc.

Thus, in one embodiment, the invention may relate to single units of a target, wherein said single units are single target molecules. In another embodiment the invention may relates to single units of a target being single individual parts of a molecule, e.g. an epitope. In another embodiment the invention may relate to a plurality of single molecular aggregates/complexes, e.g. cellular receptors comprising two associated single protein molecules of the same target protein, e.g. Her receptor or G protein-coupled receptor dimers.

Non-limiting examples of single units of a target may be single biological molecules (proteins, nucleic acids, carbohydrates, etc.), single particles (viruses), single individual molecular or cellular complexes (cellular receptors or chromatin units), single individual molecular or cellular structures (functional domain of proteins, single nucleotide polymorphisms (SNPs), epitopes, Z-fingers, PDZ-domains, proteolytic complexes etc.), or single virus particles or single microorganisms, or single fragments of said molecules, particles, complexes, structures viruses or microorganisms.

In one preferred embodiment, the target is a biological marker related to cancer, e.g. nucleic acids and polypeptides of hormones and growth factors and their receptors, cell adhesion molecules signal transduction molecules, cell cycle regulation molecules, etc, e.g. genes, RNAs and proteins of the group including growth factors PDGF, VEGF, TGF, HGF or EGF, their receptors and the pathway related molecules, genes and their products relating to signal transduction pathways, e.g. the JAK/STAT pathway or Akt1/PKB cell survival pathway, or 5-FU pathway, estrogen receptor ER and its gene (ERS1), etc. In one embodiment a target is a Her receptor or a Her receptor complex (e.g. Her2-Her3 dimer), or a fragment, structural or functional domain of a Her receptor, or a nucleic acid relating to thereof.

The methods of the invention allow visualizing and quantifying single individual units of a target present in a histological sample in a broad dynamic range. In some embodiments single units of a target may be distributed substantially homogeneously throughout a sample, in other embodiments single units of a target may be more abundant in one part of a sample and less abundant in other parts thereof. In all the latter embodiments, a population of single units of the target may be visualized as distinct dots and the amount of the target in the sample quantified, and the rest of the target units may be visualized as a homogeneous stain of a uniform pattern allowing to microscopist allocating the target to certain regions of the tissue sample.

The methods of the invention in different embodiments may comprise visualization of one target in a sample or two or more different targets in one sample by using two different target-directed staining methods, wherein first staining method visualizes single target units of a minor sub-population of the target, or a sub-population of a first target as distinct dots of color or fluorescent or luminescent light, and second staining method visualizes the bulk of the target units (i.e. the residual non-visualized by the first method target units or a sub-population of thereof), or a second target (or a sub-population of said second target) as a uniform staining pattern of homogeneous color. Thus, in some embodiments, the invention relates to visualization of fractional sub-populations of single target units present in a sample.

The term "fractional subpopulation of target (units)" in the present context means a portion of the total population of single target units that is less than 100% of the total quantity of single units of the target in the sample, e.g. equal or less than 99.9%. e.g. equal or less than 98%, 97%, 95%, 94%, 93%, 92%, 91% or 90%, such as between 90% and 85%, less than 85%, e.g. 85%-80%, 80%-75% of the total quantity of units of the target in the sample, such as less than 75%, for example from 1% to 74% of the total quantity of single units of the target in the sample, such as from 1% to 60%, 1% to 50%, 1% to 40%, 1% to 30% or 25% of the total quantity of units of the target in the sample, etc. A fractional sub-population single target units that is represented by 50%-99.9% of the total population is regarded according to the invention as a major sub-population of single target units present in the sample or the bulk of the target units. A fractional sub-population that is less than 50% of the total population of single target units in the sample is regarded herein as a minor sub-population of single target units present in the sample or a minority of the target units.

The invention preferably relates to histological samples, wherein a target is immobilized, i.e. prevented from freedom of movement during a detection and visualization procedure according to the present invention. In some embodiments, the invention relates to histological samples where the target motion is substantially reduced or eliminate by mechanical or chemical means. Samples of fresh or fixed solid body tissues or solid tumors, or samples where the target is attached onto or within a certain support or medium are non-limiting examples of the latter.

Target visualization steps of the methods of the invention may require a series of sample treatment steps preceding the visualization which may be conducted on a tissue section mounted on a suitable solid support for microscopic inspection, or the production of photomicrographs, e.g., a glass slide or other planar support, to highlight by selective staining certain morphological indicators of disease states or detection of biological markers. Thus, for example, a sample is first taken from an individual, then fixed and only then it exposed to antibodies which specifically bind to the biological marker of interest. The sample processing steps may also include other steps preceding a visualization procedure according to the invention, for example, It may involve the steps of: cutting and trimming tissue, fixation, dehydration, paraffin infiltration, cutting in thin sections, mounting onto glass slides, baking, deparaffination, rehydration, antigen retrieval, blocking steps, etc., Washing steps may be performed with appropriate buffers or solvents, e.g., phosphate-buffered saline (PBS), tris buffered saline (TBS), distilled water. The wash buffers may optionally contain a detergent, e.g., Tween 20. All these procedures are well-known routine procedures in laboratories.

Both of two categories of histological samples: (1) preparations comprising fresh tissues and/or cells, which generally are not fixed with aldehyde-based fixatives, and (2) preparations of fixed and embedded tissue specimens, often archived material, may be processed using methods of the invention.

Many methods of fixing and embedding tissue specimens are known, for example, alcohol fixation and formalin-fixation and subsequent paraffin embedding (FFPE).

Fixatives are needed to preserve cells and tissues in a reproducible and life-like manner. To achieve this, tissue blocks, sections, or smears are immersed in a fixative fluid, or in the case of smears, are dried. Fixatives stabilize cells and tissues thereby protecting them from the rigors of processing and staining techniques.

Any suitable fixing agent may be used, for example, ethanol, acetic acid, picric acid, 2-propanol, tetrahydrochloride dihydrate, acetoin (mixture of monomer and dimer), acrolein, crotonaldehyde (cis+trans), formaldehyde, glutaraldehyde, glyoxal, potassium dichromate, potassium permanganate, osmium tetroxide, paraformaldehyde, mercuric chloride, tolylene-2,4-diisocyanate, trichloroacetic acid, tungstic acid. Other examples include formalin (aqueous formaldehyde) and neutral buffered formalin (NBF), glutaraldehyde, acrolein, carbodiimide, imidates, benzoequinone, osmic acid and osmium tetraoxide.

Fresh biopsy specimens, cytological preparations (including touch preparations and blood smears), frozen sections and tissues for immunohistochemical analysis may be commonly fixed in organic solvents, including ethanol, acetic acid, methanol and/or acetone.

Samples of a pseudo tissue, e.g. the samples intended as control samples, may be processed in any mode as of the above.

3. Visualisation of Target

According to the invention a target in the sample is visualized immunochemically using an enzyme-mediated deposition of a detectable enzyme substrate. Accordingly, visualization of a target comprise a step wherein the target is detected in the sample using one or more agents that are capable of (i) specifically recognizing target units at sites of the sample comprising thereof, and (ii) linking an enzyme activity to said target units.

3.1. Binding Agents

The term "binding agent" in the present context relates a molecule that is capable of recognizing a unit of a target (to distinguish it from the other components of the surroundings) and directly or indirectly binding to it. In one embodiment a binding agent of the invention has a specific affinity to a target or another binding partner in the sample, i.e. the binding agent and the target are members of a specific binding pair, e.g. an antigen-antibody binding pair or antibody-antibody binding pair.

A binding agent which is an affinity partner to a target and capable of specifically binding to a unit of the target is referred herein as a first binding agent. A binding agent which has affinity to the first binding agent or to a substance chemically linked to the first binding agent (and thus is capable of binding to a unit of the target indirectly, i.e. via the first binding agent) referred herein as a second binding agent. In some embodiments, the second binding agent may have affinity to a substance chemically linked to the target. A target detection system according to the invention may comprise further binding agents, e.g. third, fourth, and further binding agents, that may be affinity partners to each other or to other components of the system.

Typically, a first binding agent or, in some embodiments, a second or third binding agent, is used to contact the sample to recognize the target, bind to it and form a complex with a single (or multiple) target unit(s). Second, third and further binding agents may be used in further steps of methods according to the invention, e.g. for recognition of deposits of detectable enzyme substrate(s) at target sites of the sample. In some embodiments, second, third and further binding agents may be used to amplify a signal associated with a target at target sites. Use of multiple binding agents adds to flexibility and sensitivity of the detection system of the invention.

A number of different specific binding pairs are known in the art, these are the pairs of two different molecules which are capable of specific binding to each other. Members of specific binding pairs suitable for use in practicing the invention may be of the immune or non-immune type.

Non-immune specific binding pairs include systems wherein the two components share a natural affinity for each other but are not antibodies. Exemplary non-immune binding pairs are biotin-avidin or biotin-streptavidin, folic acid-folate binding protein, complementary nucleic acids, receptor-ligand, etc. The invention also includes non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino)benzoic acid (DMAB), etc.

Immune specific binding pairs may be exemplified by antibody-antibody systems or hapten-anti-hapten systems. In one embodiment the immune specific binding pair of the invention may be an antibody-antibody binding pair comprising two or more antibody molecules having affinity to each other, for example a primary antibody and secondary antibody pair, wherein the primary antibody represents the first binding agent and the secondary antibody represents the second binding agent; Antibody systems comprising 3 or 4, or more antibody members may be used in another embodiment. In other embodiments of the invention the immune binding pair may be represented by a hapten-anti-hapten system. In such embodiments the first binding agent may be represented by a conjugate comprising a molecule having affinity to the target and a hapten, e.g. a primary antibody or nucleic acid sequence linked to a hapten, and the second binding agent may be represented by an anti-hapten antibody.

The term "hapten" designates a small molecule which can be considered as an isolated epitope to which an antibody can be made, although the hapten alone will not induce an immune response if injected into an animal, it must be conjugated to a carrier (usually a protein). As haptens are small molecules, multiple copies of a hapten may be attached to a large molecule, e.g. a polymer molecule, such as protein, nucleotide sequence, dextran, etc. Haptens may serve as convenient label molecules for assay formats where it is necessary or advantageous to amplify a signal. Thus, the bound multiple copies of a hapten provide for enhanced sensitivity, e.g. increased signal strength. Non-limited examples of suitable haptens include Fluorescein (FITC), 2,4-Dinitrophenol (DNP), myc Digoxigenin (DIG), tyrosine, nitrotyrosine biotin and dyes. e.g. tetramethylrhodamine, Texas Red, dansyl, Alexa Fluor 488, BODIPY FL, lucifer yellow and Alexa Fluor 405/Cascade Blue fluorophores, Haptens are described in US20080305497 may also be used for the purposes of the invention.

The term "antibody", as used herein, designates an immunoglobulin or a part thereof, and includes any polypeptide comprising an antigen binding site regardless of the source, method of production, and other characteristics. The term includes for example, polyclonal, monoclonal, monospecific, polyspecific, humanized, single chain, chimeric, synthetic, recombinant, hybrid, mutated, and CDR-grafted antibodies. A part of an antibody can include any fragment which can still bind antigen, for example, an F(ab)$_1$, F(ab')$_2$, Fv, scFv. The origin of the antibody is defined by the genomic sequence irrespective of the method of production.

Primary antibody, in context of the present invention, refers to an antibody binding agent, e.g. a whole antibody molecule, a fragment or a derivative of said molecule, e.g. a conjugate comprising an antibody or a polymerized antibody, that specifically binds to a target, more specifically to a single unit of a target of a sample, e.g. to a single target molecule. In some embodiments, a primary antibody may be a bivalent antibody which is capable of binding to two (or more) single individual units of different targets, e.g. an antibody that is capable of binding to a receptor dimer, e.g. Her2/Her3 dimer. In this embodiment the single unit of a target according to the invention is a single Her2/Her3 dimer, and the target is a population of Her2/her3 dimers in a sample including all said dimers of the sample. Primary antibodies may be derived from any warm blooded species, e.g. mammals, birds.

Secondary antibody, in context of the present invention, refers to an antibody binding agent, e.g. a whole antibody molecule, a fragment or a derivative of said molecule, e.g. a conjugate comprising an antibody or a polymerized antibody, that has an antigen binding domain that specifically binds to the primary antibody, or a hapten deposited in the target site, or hapten linked directly or indirectly to a primary antibody or another binding agent.

Tertiary antibody, in context of the present invention, refers to an antibody binging agent, e.g. a whole antibody molecule, a fragment or a derivative of said molecule, e.g. a conjugate comprising an antibody or a polymerized antibody that comprise an antigen binding domain that specifically binds to a secondary antibody or a hapten linked to a secondary antibody or a hapten linked to polymer conjugated to a secondary antibody, or hapten deposited in the target site.

Sometimes an antibody may function both as a secondary and a tertiary antibody.

Antibodies used in the invention, including primary antibodies, secondary antibodies and tertiary antibodies, may be derived from any mammal species, e.g., a rat, a mouse, a goat, a guinea pig, a donkey, a rabbit, horse, lama, camel, or any avian species e.g., chicken, duck. Derived from any mammal or avian species, as used herein, means that at least a part of the nucleic acid sequence encoding a particular antibody originated from the genomic sequence of a specific mammal, e.g., a rat, a mouse, a goat, or a rabbit or a specific bird e.g., chicken, duck. The antibody may be of any isotype, e.g., IgG, IgM, IgA, IgD, IgE or any subclass, e.g., IgG1, IgG2, IgG3, IgG4.

In certain embodiments a primary antibody contains an antigen binding region which can specifically bind to a biological marker, in particular to a single individual unit of said biological marker, expressed by cells of a biological sample. The marker may be expressed on the cell surface or within the cell membrane, i.e., on the interior of the cell, e.g., within the cytoplasm, within the endoplasmic reticulum, etc. In some embodiments the biological marker may be extracted from the cell and thus it is present in a cell-free medium, e.g. in an aqueous solution, or it is a soluble molecule present in a cell culture media, blood plasma, cerebrospinal fluid, etc. Examples of the corresponding samples are described above.

In certain embodiments, a secondary antibody contains an antigen binding region which specifically binds to a primary antibody, e.g., to the constant region of the primary antibody. In certain embodiments, a secondary antibody may be conjugated to a polymer. In some embodiments, 2-20 secondary antibodies, such as 5-15 secondary antibodies may be conjugated with a polymer. In other embodiments, a polymer may be conjugated with 1-10 secondary antibodies, such as 1, 2, 3, 4, 5, 6, 7, 8, 9 or 10 secondary antibodies.

In certain embodiments, a tertiary antibody may contain an antigen binding region which specifically binds to a secondary antibody, e.g., to a constant region of a secondary antibody, or to a hapten linked to a secondary antibody, or to a polymer conjugated with a secondary antibody. In certain embodiments, a tertiary antibody is conjugated to a polymer. In some embodiments, 1-20 tertiary antibodies may be conjugated a polymer. In other embodiments, 1-5 tertiary antibodies, such as 1, 2, 3, 4 or 5 tertiary antibodies may be conjugated with a polymer.

In some embodiments, polymers comprising a single binding unit of a binding agent, e.g. a polymer conjugated with one molecule of primary, secondary or tertiary antibody, may be preferred.

Antibodies that may be used for the purposes of the invention include monoclonal and polyclonal antibodies, engineered antibodies including chimeric, CDR-grafted and artificially selected antibodies produced using phage display or alternative techniques.

Antibody binding agents of the invention may be produced by any of numerous methods well-known in the art e.g., according to Harlow and Lane, *Antibodies: a Laboratory Manual*, (1988) (Cold Spring Harbor Press, Cold Spring Harbor, N.Y.). Techniques for the preparation of recombinant antibody molecules are described in the above reference and a number of other references, e.g., EP 0623679; EP 0368684; and EP 0436597. Nucleic acids encoding antibodies may be isolated from a cDNA library. Nucleic acids encoding antibodies may be isolated from a phage library (see e.g. McCafferty et al. 1990, *Nature* 348:552, Kang et al. 1991, *Proc. Natl. Acad. Sci. USA* 88:4363; EP 0 589 877 B1). Nucleic acids encoding antibodies can be obtained by gene shuffling of known sequences (Mark et al. 1992, *Bio/Technol.* 10:779). Nucleic acids encoding antibodies can be isolated by in vivo recombination (Waterhouse et al. 1993, *Nucl. Acid Res.* 21:2265). The antibodies used in the methods of the invention include humanized immunoglobulins (see U.S. Pat. No. 5,585,089, Jones et al. 1986, *Nature* 332:323). Antibodies of the invention may be altered any possible way, presuming that they retain their binding affinity, e.g, they may fused with an effector protein, toxin, label, etc. Methods of conjugation of antibody with different agents are also well known in the and described in exemplary embodiment of the invention below.

In one embodiment of the invention, an antibody binding agent is represented by the Fab region, i.e. $F(ab)_1$ or $F(ab)_2$.

In one embodiment an antibody binding agent may be a composition comprising two or more different antibody binding agents, e.g., a composition comprising a first antibody binding agent and a second antibody binding agent, wherein the two or more different antibody agents are of different immune binding pairs. In one embodiment, in the composition, at least one of the two or more different antibody binding agents of is an antibody that is capable of specifically binding to a target and at least one another is an antibody which comprises a an enzyme.

In another embodiment, the invention may relate to binding agents that are members of non-immune specific binding pairs, such as complementary nucleotide sequences, or nucleic acid analog molecules.

A binding agent comprising a nucleic acid or nucleic acid analog molecule, e.g., a DNA molecule, an RNA molecule, a PNA molecule, may be useful for the visualization and quantification of single individual units of nucleic acid targets.

Nucleic acid sequences used as binding agents for the purposes of the invention may be synthesized chemically or produced in recombinant cells. Both modes of production are well known in ht eart (see e.g. Sambrook et al. (1989) *Molecular Cloning: A Laboratory Manual*, 2nd ed. Cold Spring Harbor Press). In some embodiments, a nucleic acid binding agent may comprise a peptide nucleic acid (PNA). A peptide nucleic acid is a nucleic acid molecule in which the deoxyribose or ribose sugar backbone, usually present in DNA and RNA is replaced with a peptide backbone. Methods of making PNAs are known in the art (see e.g. Nielson, 2001, *Current Opinion in Biotechnology* 12:16) (hereby incorporated by reference). In other embodiments, the binding agent may comprise a locked nucleic acid (LNA) (Sorenson et al. 2003, *Chem. Commun.* 7(17):2130).

A nucleic acid binding agent, in some embodiments, may comprise at least one oligo nucleotide or at least one polynucleotide sequence that specifically hybridizes to a single unit of a target sequence in a biological sample, e.g. a single mRNA sequence, under specific conditions of stringency. The term "hybridization under stringent conditions," is used herein to describe conditions for hybridization under which nucleotide sequences that are significantly complementary to each other, such as at least 70%, at least 80%, at least 85-90% complementary, remain bound to each other. The percent complementary is determined as described in Altschul et al. (1997) *Nucleic Acids Res.* 25:3389-3402 (hereby incorporated by reference).

Specified conditions of stringency are known in the art and can be found in *Current Protocols in Molecular Biology*, John Wiley & Sons, Inc. (Ausubel et al. 1995 eds.), sections 2, 4, and 6 (hereby incorporated by reference). Additionally, specified stringent conditions are described in Sambrook et al. (1989) *Molecular Cloning: A Laboratory Manual*, 2nd ed. Cold Spring Harbor Press, chapters 7, 9, and 11 (hereby incorporated by reference). In some embodiments, the hybridization conditions are high stringency conditions. An example of high stringency hybridization conditions is hybridization in 4× sodium chloride/sodium citrate (SSC) at 65-70° C. or hybridization in 4×SSC plus 50% formamide at 42-50° C., followed by one or more washes in 1×SSC, at 65-70° C. It will be understood that additional reagents may be added to hybridization and/or wash buffers, e.g., blocking agents (BSA or salmon sperm DNA), detergents (SDS), chelating agents (EDTA), Ficoll, PVP, etc.

In some embodiments, the binding agents may hybridize to a target sequence in a sample under moderately stringent conditions. Moderate stringency, as used herein, include conditions that can be readily determined by those having ordinary skill in the art based on, for example, the length of the DNA. Exemplified conditions are set forth by Sambrook et al. *Molecular Cloning: A Laboratory Manual*, 2d ed. Vol. 1, pp. 1.101-104, Cold Spring Harbor Laboratory Press (1989) (hereby incorporated by reference), and include use of a prewashing solution of 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

In some embodiments, the binding agents hybridize to a target sequence in a sample under low stringent conditions. Low stringency conditions may include, as used herein, conditions that can be readily determined by those having ordinary skill in the art based on, for example, the length of the DNA. Low stringency may include, for example, pretreating the DNA for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and $5-20 \times 10^6$ CPM binding agent is used. Samples are incubated in hybridization mixture for 18-20 hours at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C.

In other embodiments the invention may relate to binding agents that are peptide sequences or comprise peptide sequences that are derived from non-antibody proteins, e.g. peptide sequences derived from nucleic acid binding domains of different proteins, ligands of different cellular and nuclear receptors and their derivatives. Some non-limiting examples of such binding agents may be c1q protein of the classical pathway of the complement cascade which can bind to an antibody constant region, a MHC molecule, e.g., MHC class I and MHC class II and non conventional MHC, a molecule having a specific binding partner, such as molecules involved in cellular signaling pathways such as molecules having leucine zipper domains, e.g., fos/jun, myc, GCN4, molecules having SH1 or SH2 domains, such as Src or Grb-2; an immunoglobulin receptor, e.g., an Fc receptor; a chimeric protein, i.e., a protein engineered to combine the features of two or more specific binding partners, e.g., a leucine zipper could be engineered into a Fc region of an antibody, an SH2 domain could be engineered to be expressed in a Fc region of an antibody. In other embodiments, fusion proteins can be engineered comprising an Fc portion of an antibody with a substituted variable domain.

The binding agent may also be small molecules which can bind specifically to certain structural units of large biological molecules.

Embodiments of the invention include binding agents that comprise detectable labels, e.g. fluorescent substances, haptens, enzymes, etc. Use of such labeled binding agents is a part of visualization target units at sites of the sample comprising thereof, in particular enzyme-labeled binding agents are used to link the enzymatic activity to the target. In one embodiment, the invention relates to a first binding agent comprising an enzyme, in another preferred embodiment the invention relates to a second binding agent comprising an enzyme, in another embodiment the invention relates to a third bind agent comprising an enzyme, In one embodiment, the invention relates to two or more binding agents comprises in a target visualization system described herein, e.g. a second and a third binding may comprise an enzyme. Enzyme linked to the binding agents may be the same enzyme, e.g. horseradish peroxidase (HRP), or it may be different enzymes, e.g. HRP and alkaline phosphatase (AP). In one preferred embodiment, the second binding agent, or third binding agent or a further binding agent is an antibody conjugated with an enzyme. In another preferred embodiment, the binding agents are probes for detection of nucleic acids which are conjugated with an enzyme.

Non-limiting examples of suitable enzyme labels may be horseradish peroxidase (HRP), alkaline phosphatase (AP), beta-galactosidase (GAL), glucose-6-phosphate dehydrogenase, beta-N-acetylglucosaminidase, ß-glucuronidase, invertase, xanthine oxidase, firefly luciferase, glucose oxidase (GO), or derivatives of these enzymes. In one preferred embodiment a binding agent may comprise HRP or a derivative thereof. In another preferred embodiment, a binding agent may comprise AP or a derivative thereof. Embodiments of enzyme labels are also discussed below.

Amounts of binding agents used at different steps of target visualization procedures may vary depending on different factors, e.g. sample species, target species, binding agent species, binding affinity of binding agents, etc. Using common general knowledge the skilled in the art can select an appropriate binding agent and determine the amount needed for every particular embodiment (a detailed guidance may be found e.g. in Harlow and Lane, *Antibodies: a Laboratory Manual*, (1988) Cold Spring Harbor Press, Cold Spring Harbor, N.Y.; or in Harlow, Lane, *Using Antibodies: A Laboratory Manual*, (1999) Cold Spring Harbor Press, Cold Spring Harbor, N.Y.

In one embodiment, it may be preferred that the amounts of binding agents used for detecting target units in the sample and linking then to an enzyme activity are so that only a minor fractional sub-population of units of the target is detected and linked to the enzymatic activity. Such conditions are preferable for visualizing individual target units as distinct dots, wherein the distinct dot corresponds to a deposit of a detectable enzyme substrate generated by an enzymatic activity linked to a single target unit. In other embodiments, it may be preferred that majority of units of a target detected and linked to an enzymatic activity using one or more binding agents. In these embodiments it may be preferred to use the saturating amounts of one or more binding agents. In such conditions sites of the sample comprising the target are visualized as a uniform pattern of homogeneous color corresponding to the color of deposited enzyme substrate In one embodiment, a binding agent may be a mixture of unlabelled and labeled binding molecules of the same species that have affinity to the same binding partner, e.g. a mixture of labeled and unlabelled primary antibody to a particular target protein, or a mixture of labeled and unlabelled secondary antibody against a particular species of primary antibodies, or the like. According to the invention, using the latter mixtures of binding molecules, wherein a portion of the labeled binding molecules is predetermined, the target sites formed (and then visualized as visually distinct dots) with a certain fractional sub-population of single target units that is predetermined by the portion of the labeled binding agent. This allows determining the precise quantity of single target units in the sample, and, thus, the quantity of the target, including a relative and total amount of the target in the sample. Methods of quantification of targets in histological samples visualized by a method of the invention are described in PCT/DK2011/000131 (incorporated herein by reference).

3.3. Enzyme

According to the invention a target in a histological sample is visualized by generating a stain at sites of the sample, wherein the sites comprise the target. The stain is generated via one or more enzyme-mediated depositions of one or more detectable substrates, wherein at least one of the deposited substrates is the stain. According to the invention the target-comprising sites of the sample are linked to an enzymatic activity by using at least one binding agent comprising an enzyme that directly or indirectly binds to a target unit and forms a complex with said unit.

In one embodiment, the enzyme associated with a target site according to the invention is an enzyme with oxidoreductase activity.

By the term "enzyme with oxidoreductase activity" is meant an enzyme classified as EC 1 in the EC number classification of enzymes that catalyzes the transfer of electrons from one molecule (the reductant, also called the hydrogen or electron donor) to another (the oxidant, also called the hydrogen or electron acceptor). In some preferred embodiments, the invention relates to oxidoreductases classified as E 1.10. (phenoloxidases) and E 1.11. (peroxidases).

In one preferred embodiment the invention relates to phenoloxidases, in particular to the family of copper-containing oxidase enzymes, laccases (E 1.10.3.2). Laccases act on phenols and similar molecules, performing one-electron oxidation. Laccases play a role in the formation of lignin by promoting the oxidative coupling of lignols, a family of naturally occurring phenols. A laccase suitable for the purposes of the invention may be for example an enzyme described by Phillips L E and Leonard T J (Benzidine as a Substrate for Measuring Phenoloxidase Activity in Crude Cell-Free Extracts of Schizophyllum commune. Mycologia 1976, 68: 277-285), or Kunamneni A, Plou F J, Ballesteros A, Alcalde M. (Laccases and their applications: a patent review. Recent Pat Biotechnol. 2008, 2(1):10-24), or Rodriguez Couto S, Toca Herrera J L (Industrial and biotechnological applications of laccases: a review. Biotechnol Adv. 2006, 24(5):500-13.)

In another preferred embodiment, the invention relates to a peroxidase enzymatic activity catalyzing a reaction of the form: $ROOR'+\text{electron donor }(2\ e^-)+2H^+ \rightarrow ROH+R'OH$.

In one preferred embodiment of the invention, the enzyme with peroxidase activity is horseradish peroxidase (HRP). In another embodiment of the invention, the enzyme with peroxidase activity is soyabean peroxidase (SP).

For some peroxidases the optimal substrate is hydrogen peroxide, some others are more active with organic hydroperoxides such as organic peroxides. The nature of the electron donor is very dependent on the structure of the enzyme, e.g. horseradish peroxidase (HRP) can use a variety of organic compounds both as electron donors and acceptors. HRP has an accessible active site, and many compounds can reach the site of the reaction.

The oxidireductase enzymatic activity associated with a target site of the sample may be represented by a full-length molecule of an enzyme which is directly or indirectly linked to the molecule of a binding agent, or a fragment of the enzyme conflated with the enzymatic activity, e.g. 51% to 99.9% of the full size of the enzyme molecule, or less than 51%, e.g. 40%, 30% or less.

A binding agent of the invention may be directly or indirectly conjugated with one or more enzyme moieties, (the term "moiety" in the present content means a part of molecule of the enzyme that is capable of oxidoreductase activity, it includes both entire or substantially entire enzyme molecule and portions of said molecule that are capable of oxidoreductase enzymatic activity). Molecules of both or either first and/or second binging agents may be conjugated with one or several functionally active moieties of an oxidoreductase. In one embodiment at least one molecule of a first binding agent may be conjugated with one or more enzymatic moieties capable of oxidoreductase activity; in another embodiment at least one molecule of a second binding agent may be conjugated with one or more such moieties. Molecules of third and further binding agents may also be conjugated with an oxidoreductase. The term "directly conjugated" means that an enzyme moiety is linked to a molecule of a binding agent via a chemical bond. The term "indirectly conjugated" means that a moiety of an enzyme is linked to the molecule of a binding agent via a linking molecule, which has one chemical bond with binding agent and another chemical bond with the enzyme. Methods of conjugating biological molecules and linker molecules are well-known in the art and exemplified below.

In one embodiment the moiety of oxidoreductase is a moiety of HRP, e.g. the whole HRP molecule a fragment thereof that is capable of the HRP enzymatic activity, it may also be a recombinant protein comprising the part of HRP that possesses the enzymatic activity, etc. In another embodiment the moiety of oxidoreductase may be a moiety of soybean peroxidase (SP). In another embodiment the moiety of oxidoreductase may be a moiety of laccase.

Non-limiting examples of binding agents which comprise an enzyme with oxidoreductase activity may be antibody molecules or derivatives thereof, e.g. a Fab, e.g. F(ab)1 or F(ab)2, conjugated with one or more moieties of HRP, and nucleic acid binding agents conjugated with HRP. Such binding agents may bind directly or indirectly to single target units, e.g. single target molecules, and form thereby complexes, wherein a single such complex comprises a single individual unit of the target and one or more of binding agents wherein one or more of the binding agents comprise an enzyme with oxidoreductase activity.

In one embodiment the binding agent may be a conjugate comprising one, or two or more moieties of a peroxidase wherein said moieties are chemically linked to the binding agent, e.g. an antibody molecule conjugated with one or more moieties of HRP, a conjugate wherein one or more molecules of an antibody and one or more HRP moieties independently linked to a backbone polymer.

The number of enzyme moieties (e.g. HRP) per molecule of a binding agent may vary, from 1 to 20-50 per a binding agent or be even higher. In some embodiments it may be preferred to use binding agents wherein the number of enzyme moieties is at least two, preferably from two to twenty-twenty five enzyme moieties per binding agent, e.g. between three and twenty, such as 4, 5, 6, 7, 8, 9, 10 etc. In some embodiments it may be preferred to use binding agents comprising more than four enzyme moieties per binding agent per binding agent, preferably between 5 and 20, for example from 5 to 15. Binding agents with more than four enzyme moieties are favorable for formation of target sites which can be visualized as substantially identical in size dots. In some embodiments, it may be preferred to use a pool of binding agent molecules comprising 4-6 enzymes per binding agent molecule or 5-7, 6-8, 7-9, 8-10, etc, e.g. 5-6 or 6-7 HRP moieties per an antibody molecule. Molecules of binding agents in some embodiments may also comprise combinations of multiple moieties of different oxidoreductase enzymes.

In some embodiments, relatively small conjugate molecules of binding agents, e.g. single antibody molecules or isolated Fab regions of antibodies that are conjugated with one, or two, or more moieties of an enzyme, e.g. HRP, may be preferred. Such binding agents are relatively compact molecules and this may be advantageous for detecting individual units of targets that are "hidden" or masked in a target or in a sample, e.g. individual single target molecules may be masked by other molecules of the surroundings, single target structures can be hidden in a target molecule, or single viral particles may be hard to reach in complicated biological samples comprising cells.

In some other embodiments, large conjugates comprising a binding agent and tens to hundreds enzyme moieties may be preferred. Such binding agents may be advantageous e.g. in cases where very fast target detection is concerned or obtaining large deposits per individual target site is desirable.

In one embodiment a binding agent may comprise one or more moiety of Alkaline phosphatase (AP). The above discussed embodiments of binding agents an enzyme with oxidoreductase activity are applicable to binding agents comprising AP.

3.4. Deposition of Stain

A target in histological samples may be visualized according to the invention by:
a) Immunochemically staining the sample with a first stain, and
b) Immunochemically staining the sample with a second stain, wherein both the first and the second stains are generated via an enzyme mediated deposition of a detectable enzyme substrate at sites of the sample comprising the target; and wherein the first stain visualizes one or more single units of the target as distinct dots of the first stain, and the second stain visualizes the bulk of the target as a uniform staining pattern of homogenous second stain.

3.4.1. Staining with a First Stain

Staining of target sites with a first stain allows visualizing single target sites in the sample, i.e. sites comprising single target entities (e.g. single target molecules or single epitopes), as distinct dots of the first stain (see WO2011047680 and PCT/US2011/6242). It is surprisingly found that the size and optical characteristics of the dots make them clearly distinguishable on the background of a histological staining and on the background of a conventional IHC stain that has a uniform staining pattern. By "uniform staining pattern" is meant that the staining appears to a microscopist as even and homogeneous color without apparent resolution into staining parts making the staining. Typically, a homogeneous color pattern provided by a conventional IHC marks sites of the sample that comprise a target with intracellular resolution of cellular structures, e.g. membrane, cytoplasm, and nucleus, and does not allow distinguishing individual single units of the target. The dots provided by staining with a first stain are distinguishable even in embodiments when a conventional IHC stain providing a uniform staining pattern. This advantage is used in the methods of the invention and the same target (or a second target) is, in one embodiment, visualized using staining with a second stain that provides a uniform staining pattern.

Using well-defined binding agents, as discussed above, IHC staining (a) allows visualizing single target units of a fractional sub-population of target units comprising one single target unit, a few single units, and up to about 50% of all target units in a sample. In some embodiments, the total population of single target units may be visualized by staining (a) (e.g. a low expression target). The rest of target units, i.e. target units that were not bound to a binding agent, marked with an enzymatic activity on step (a) and not stained with the first stain, are according to the invention eligible for visualization/detection by other suitable methods, e.g. by a conventional IHC staining, e.g. a staining based on a HRP or AP-mediated deposition of the corresponding detectable substrates.

A staining of a population of target sites as distinct dots in one embodiment may be performed according to the procedures described in WO2011047680. The term "distinct"<dot> is meant that a dot of stain at a target site has particular optical and physical features, e.g. roundness, hue, sharpness, size, etc. that make it distinguishable from both stained and unstained material in the sample.

Accordingly, in one embodiment of the present invention, visualization of a target in a histological sample with a first stain may comprise the following steps:
a) incubating the sample comprising a population of individual units of a target with of one or more binding agents, wherein
(1) at least one of the binding agents comprises an enzyme with oxidoreductase activity;
(2) at least one of the binding agents is capable of directly binding to an individual single unit of the target,
and forming one or more discrete single target sites a fractional sub-population of individual single units of the target, wherein each single discrete single target site comprises a complex of one individual single unit of said fractional sub-population and one or more binding agents, at least one thereof comprising the enzyme;
b) incubating a sample of (a) in an aqueous solution (A) comprising
a peroxide compound in an amount that is less than 2 mM,
a first substrate of the enzyme associated with discrete single target sites of (a) and,
a second substrate of said enzyme,
wherein said first substrate is a water soluble electron rich organic compound which is
(1) capable of generating a radical upon a reaction with said enzyme; and
(2) capable of cross-linking molecules of said second substrate in the presence of both said enzyme and a peroxide compound, thereby producing a water insoluble polymeric product of said second substrate,
and wherein said second substrate is a conjugate molecule comprising at least two compounds that are capable of serving as substrates of said enzyme and a detectable label, wherein the detectable label is selected from the group consisting of a fluorescent, luminescent, radioactive or chromogenic matter and a member of a specific binding pair,
thereby forming discrete deposits of the second substrate at discrete single target sites of (a) and visualizing said single target sites of (a) as discrete optically distinguishable dots of stain.

In one preferred embodiment, the enzyme associated with single target units is HRP. Embodiments of the first substrate of the enzyme include but not limited to 3'3'-diaminobenzidine, ferulic acid and alpha-cyano-4-hydroxycinnamic acid. Other suitable compounds as the first substrate may be generally described by the formula (I):

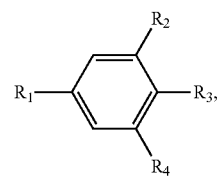

wherein
R1 is an aryl or vinyl,
R2, R3 and R4 is independently H, N—$(X)_2$, O—$(X)_2$, wherein X is an alkyl, vinyl or aryl, or H, and wherein R2, R3 and R4 are not simultaneously H, wherein.
N is nitrogen,
H is hydrogen;
O is oxygen.

A second substrate of the enzyme associated with a target site may be selected from a large group of conjugate molecules that share the following features:
1. The conjugate molecules are water soluble molecules comprising two or more substances that can serve as substrates of the enzyme of the invention, preferably as substrates of HRP, and one or more labels wherein the substrates and labels are linked together via a water soluble linker compound (termed hereafter "linker");
2. The enzyme substrate moieties are "concentrated" in the conjugate molecule in one part of said molecule and the labels are "concentrated in another part of said molecule, wherein the label(s) are distanced away from the substrates by approximately 30 consecutively interconnected atoms or more, i.e. separated approximately by 2.5 nm or more, preferably by more than 3 nm 3. The enzyme substrates are separated from each other by a distance that is less than 2.5 nm, e.g. separated within molecule of the conjugate by less than 30 interconnected carbon or heteroatoms, such as carbon, nitrogen, sulphur and/or oxygen atoms or less, preferably not more than 5-20 atoms;
4. The linker is a compound which comprises at least 30 consecutively connected atoms;
5. The conjugates do not precipitate from an aqueous solution (ii) containing a peroxide compound and a first substrate of the invention in the absence in the environment of an enzyme with oxidoreductase activity.
6. The conjugates do not precipitate from an aqueous solution (ii) containing a peroxide compound in the presence of an enzyme with oxidoreductase activity and in the absence the first substrate of said enzyme in the environment.
7. The conjugates precipitate from an aqueous solution (ii) containing a peroxide compound and the first substrate of an enzyme with oxidoreductase activity of the invention in the presence of said enzyme in the environment.

Deposits of second substrate may be directly optically detectable as distinct dots because, in some embodiments, the second substrate may comprise a chomogenic, fluorescent or luminescent label. In other embodiments, the deposits of second substrate at target sites may be "stained" in steps following the deposition. Staining of optically "invisible" deposits of the second substrate make done using a routine method for immunostaining comprising (i) detecting the deposit with an affinity binding agent; (ii) "marking" the deposit with an enzyme activity (e.g. HRP or AP); and (iii) depositing at the deposit site a detectable enzyme substrate. The deposit may also be stained by repeating the procedure for deposition of a second enzyme substrate at the target site with another second substrate that is optically detectable. In any of the cases, the deposits of the second substrate in the sample will "report" the presence of target sites that comprises singe unities of the target. Accordingly, the molecules of second substrate of the invention are also termed herein as "reporter" molecules.

In one embodiment the invention relates to a second substrate which is a water soluble conjugate molecule that comprises
   (i) one or more detectable substances (termed interchangeably "label")
   (ii) at least two substances, which are capable of serving as substrates of the enzyme of the invention, and
   (iii) a linker
      wherein
      said linker is a compound comprising at least one linear chain consisting of at least 30 consecutively connected atoms that contains at least two branching points, wherein said brunching points are separated by a molecular distance of at least 30 consecutively connected atoms;
      wherein
      the labels (i) and oxidoreductase substrate moieties (ii) are attached to the linker at its two branching points that are separated by a distance of at least 30 consecutively connected atoms, and
      wherein
      any two neighboring enzyme substrates are separated from each other by a molecular distance that is less than 30 consecutively interconnected atoms.

In one embodiment, conjugate molecules of the invention may be selected from a group of compounds of formula (II):

$(Y)_n\text{-}L\text{-}(Z)_m$, wherein
Y is a moiety capable of serving as substrate of an enzyme with oxidoreductase activity;
Z is a detectable label;
L is a linker compound
wherein
n is an integer from 2 to 150, and
m is an integer from 1 to 150

In one preferred embodiment Y is selected from compounds of the following formula (II):

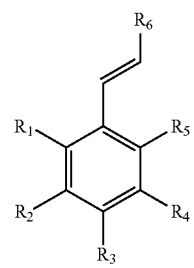

wherein
R1 is —H, —O—X, N(X)$_2$ or —S—X;
R2 is —H, —O—X, —N(X)$_2$, or —S—X,
R3 is —H, —OH, —NH$_2$ or —SH;
R4 is —H, —O—X, —N(X)$_2$, or —S—X,
R5 is —H, —O—X, N(X)$_2$, or —S—X,
R6 is —CON(X)$_2$, or CO—X,
wherein
   H is hydrogen;
   O is oxygen
   S is sulphur
   N is nitrogen, and
   X is H, alkyl or aryl.

In one embodiment at least one of the compounds that are capable of serving as substrate of an enzyme with oxidoreductase activity is a compound of formula (ii).

In one embodiment at least two of the compounds that are capable of serving as substrate of an enzyme with oxidoreductase activity in the conjugate molecule are compound of formula (ii).

In one embodiment at least two of the compounds that are capable of serving as substrate of an enzyme with oxidoreductase activity in the conjugate molecule are identical compounds of formula (ii).

In one embodiment at least two of the compounds that are capable of serving as substrate of an enzyme with oxidoreductase activity in the conjugate molecule are different compounds of formula (ii).

In one embodiment all compounds that are capable of serving as substrate of an enzyme with oxidoreductase activity in the conjugate molecule are defined by formula (II). In one embodiment these are identical compounds, in another embodiment the conjugate molecule comprises any combination of different compounds defined by formula (II).

In one preferred embodiment Y may be a residue of cinnamic acid; in another preferred embodiment Y may be a residue of ferulic acid. In another preferred embodiment Y may be a residue of caffeic acid; in another preferred embodiment Y may be a residue of amino cinnamic acid. In another preferred embodiment Y may be a residue of sinapinic acid. In another preferred embodiment, Y may be a derivative of ferulic acid, cinnamic acid, caffeic acid, amino cinnamic acid or sinappinic acid.

Preferably a residue Y defined by the formula (II) is connected to a linker L via group R6.

In one preferred embodiment the conjugate comprises two to four identical residues Y. In another preferred embodiment the conjugate comprises a combination of two to four different residues Y. In one preferred embodiment the two to four residues Y are compounds defined the formula (II).

In one preferred embodiment, the conjugate may comprise two to four residues ferulic acid or residues of derivatives thereof, in another embodiment the conjugate may comprise two to four residues cinnamic acid or residues of derivatives thereof; in another embodiment the conjugate may comprise two to four residues of caffeic acid or residues of derivatives thereof; in another embodiment the conjugate may comprise two to four residues amino cinnamic acid; in another embodiment the conjugate may comprise two to four residues sinapinic acid or residues of derivatives thereof. The two to four derivatives of the latter compounds may be the same compound or may be different compounds.

In one preferred embodiment a conjugate molecule may comprise two Y compounds of formula (II), or two derivatives thereof, e.g. two ferulic acid residues, or two cinnamic acid residues, or two amino cinnamic acid residues, or two caffeic acid residues, or two sinapinic acid residues, etc. and one or more detectable labels; in another embodiment the conjugate may comprise three molecules of formula (II) or three derivatives thereof, such as three ferulic acid, cinnamic acid, caffeic acid, amino cinnamic acid, sinapinic acid, etc., and one or more detectable label; in another embodiment the conjugate may comprise four compounds of formula (II) or four derivatives thereof, e.g. four ferulic acid, cinnamic acid, caffeic acid, amino cinnamic acid, sinapinic acid, or four derivatives the latter, and one or more detectable labels.

In some embodiments the number of Y compounds may be higher than 4, e.g. such as 5-10, 10-15, 15-20, 20-50, 50-100, or 100-150 compounds. Non-limiting examples of such conjugate molecules are described in Examples. In some preferred embodiments such conjugates may comprise more than one linear chain of at least 30 consecutively connected atoms, e.g. 30-150 atoms, wherein two to four Y compounds are attached to each linear chain at first and the same branching point of the chain, and several of such linear chains are linked to another water soluble linker molecule, e.g. a dextran, via a second (another) branching point of said linear chains.

In one preferred embodiment, a conjugate molecule may comprise a combination of two or four different compounds of formula (II), or a combination of two or four derivatives thereof, e.g. two ferulic acid residues and one cinnamic acid residue, two sinapinic acid residues and two caffeic acid residues, etc.

In one preferred embodiment Y may be a residue of amino acid tyrosine or residue of a derivative thereof. A conjugate may comprise 2 to 4 or more such residues.

In one embodiment conjugate molecule may comprise a combination of substrates of the enzyme with oxidoreductase activity, wherein at least one of said substrates is tyrosine. In one embodiment the conjugate molecule comprises at least one tyrosine residue and at least one compound of formula (II), or a derivative thereof. and at least one another is a compound of formula (II) a derivative thereof, e.g. one tyrosine residues and two residues of sinapinic acid or derivatives thereof.

In some embodiments it may be preferred that the conjugate comprises 4 to 6 residues Y, wherein Y is represented by any compound or a combination of any compounds as described above.

Y compounds may be located in a conjugate molecule as a group, preferably grouped as two to four Y compounds per group, (i.e. a conjugate comprising more than four Y compounds may comprise several groups of two to four Y compounds, wherein said groups are separated in the conjugate molecule by a group of atoms, e.g. by a molecular distance corresponding to 30 connected atoms or more). Preferably, the two to four Y compounds in such groups are linked together via a spacer compound that provides a distance between two neighboring Y residues which is not longer than 5-15 interconnected atoms, e.g. 5-10, 6-12, 7-13, 8-14, 9-15, etc., For example, 2-4 Y compounds may be attached to amino acids making up a peptide chain comprising 2 to 4 amino acid residues, e.g. residues of lysine, serine, cystein, etc., wherein the Y compounds are attached to reactive groups of the amino acid residues of the peptide, e.g. to the epsilon amino groups of lysine residues. Two to four compounds Y may also be connected to each other via other short polymers which comprise a number of brunching points, wherein a molecular distance between these branching points corresponds to a chain of not more than 3-7 atoms, preferably 3-5 atoms, wherein the Y compounds may be directly indirectly linked to said branching points. Two to four compounds Y may also be grouped together being conjugated to a non-polimeric molecule that have two to four reactive groups allowing attaching any two to four Y compounds. Such grouped location of Y compound is termed thereafter "Y-head" of the conjugate molecule.

In one preferred embodiment, the Y-head comprises two to four Y-residues linked via a short polymer, e.g. a short PNA molecule or a short peptide, wherein the peptide, preferably, comprises lysine, serine glutamate and/or cystein residues. However, any other polymeric or non-polymeric water soluble molecules that comprise 15 or less atoms that can be conjugated with at least two Y-residues and a linker L may be suitable.

In one embodiment one Y-head comprising two to four compounds Y may be linked to a polymer comprising two or more repeats of the following formula (III)

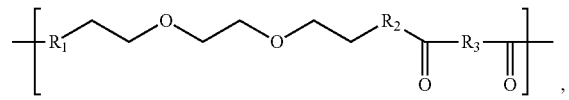

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups. The resulting conjugate may be further conjugated with one (or more) detectable label, or it may be conjugated with another water soluble molecule which comprises one or more reactive groups allowing attaching one or several such conjugates. One non-limiting example of such water soluble molecule may be a dextran polymer.

The detectable label of a conjugate molecule may be any substance which can be visually detected, e.g. a fluorescent or luminescent substance, or any substance that can be detected by using some detecting means, e.g. a radioactive label, a member of a specific binding pair, e.g. a nucleic acid sequence, hapten, etc.

Any fluorescent, luminescent, bioluminescent or radioactive molecules may be used as the labels. Many of them are commercially available, for example fluorescent stains Alexa Fluors (Molecular Probes) and DyLight Fluors (Thermo Fisher Scientific). Other non-limited examples of fluorescent labels may be the following molecules: 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, Cy2, Cy3, Cy5, AMCA, PerCP, R-phycoerythrin (RPE) allophycoerythrin (APC), Texas Red, Princeton Red, Green fluorescent protein (GFP) coated CdSe nanocrystallites, ruthenium derivatives, luminol, isoluminol, acridinium esters, 1,2-dioxetanes and pyridopyridazines, radioactive isotopes of hydrogen, carbon, sulfur, iodide, cobalt, selenium, tritium, or phosphor.

In some embodiments the detectable label may be an enzyme. Non-limiting examples of suitable enzyme labels may be alkaline phosphatase (AP), beta-galactosidase (GAL), glucose-6-phosphate dehydrogenase, beta-N-acetyl-glucosaminidase, ß-glucuronidase, invertase, xanthine oxidase, firefly luciferase, glucose oxidase (GO).

In other embodiments, the detectable label may be a member of a specific binding pair, e.g. a hapten. As non-limiting examples of suitable haptens may be mentioned 2,4-dinitrophenol (DNP), digoxigenin, fluorescein, Texas Red, tetra methyl rhodamine, nitrotyrosine, acetylaminoflurene, mercury trintrophonol, estradiol, bromodeoxy uridine, dimethylaminonaphthalene sulfonate (dansyl), amino acids tyrosine, serine, etc. As examples of suitable specific binding pairs may also be mentioned biotin, streptavidin, complementary natural and non-natural oligonucleotide sequences, zink fingers binding domain pairs, etc. Other examples are discussed above.

In one preferred embodiment the label is a hapten. In another preferred embodiment, the label is a fluorescent substance. In another preferred embodiment, the label is a member of a specific binding pair. Other labels may be preferred in other embodiments.

The number or detectable labels per conjugate molecule (as any of the described above) may vary. In some embodiments the number of labels may be from 1 to 3, for example 1, 2 or 3 labels per conjugate molecules. In some other embodiments, the conjugate may comprise more from 4 to 150 labels per conjugate molecule.

In one preferred embodiment a conjugate (as any of the described above) comprises one detectable label. In one preferred embodiment a conjugate molecule may comprise one Y-head (as any of the discussed above) and one label.

In a conjugate molecule the detectable substance (a single label or a plurality thereof) may be separated from the compounds that are substrates of an enzyme with oxidoreductase activity, e.g. from an Y-head, by a molecular distance of more than 2.5 nm, e.g. separated by a chain of at least 30 consecutive atoms, e.g. 30-150 or more consecutive atoms. In embodiments where the conjugate comprises one chain of connected atoms as L linker between an Y-head and 1 (or more) labels, the Y-head and the label(s) are linked to said chain at branching points located at least 30 atoms apart from each other, e.g. on the opposite ends of a chain of 30 connected atoms.

In some embodiments, when a conjugate comprises more than 1 label, it may be preferred that the labels are grouped so that there is a molecular distance between the labels, that correspond to a chain of at least 30 consecutively connected atoms (termed "spacer"), preferably 60 consecutively atoms or more, e.g. 90 consecutively interconnected atoms. It is preferred that the spacer between the labels is a hydrophilic compound. The latter group of labels is then attached to a linker compound linking said labels and enzyme substrate moieties in a conjugate molecule in the way described above, i.e. a label of the group that is positioned closest to the Y-head is distanced away from any of the enzyme substrates of the Y-head by at least 30 interconnected atoms, i.e. by at least 2.5 nm distance. Such arrangement of multiple labels in a conjugate molecule is termed thereafter "Z-tail".

Preferably, a spacer of at least 30 consecutive atoms between labels of a Z-tail is a polymeric compound comprising two or more repeats of the following formula (III)

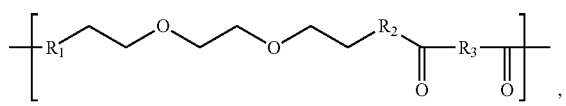

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups.

Multiple labels attached to and separated by the above spacer may be conjugated with one Y-head or several Y-heads via any suitable linker, e.g. water soluble polymers allowing multiple attachments, e.g. dextran. In some embodiments several Y-heads may be conjugated with several Z-tails via such polymer.

In one embodiment multiple labels of a conjugate molecule of the invention may be same detectable substances, in another embodiment the labels may be different detectable substances.

The linker between the oxidoreductase substrates and labels (e.g. between Y head and Z tail), L, is according to the invention a molecule that comprises a chain of at least 30 contiguous atoms, such as 30-150 atoms or more, e.g. 30, 45, 60, 90, 120. In one preferred embodiment preferably, L comprises 150 contiguous atoms. In some embodiments, a linker molecule comprises a linear chain of atoms wherein every two connected carbon atoms are followed by an atom of oxygen or nitrogen.

In one preferred embodiment L may be a single linear polymer molecule; in another preferred embodiment L may be a conjugate molecule which may comprise several different polymers conjugated together.

In one preferred embodiment L is a linear polymer that comprises a chain of atoms wherein two consecutive carbon atoms are followed by a heteroatom selected from oxygen or nitrogen, e.g. such as a linker comprising described below, or polyethylene glycol, etc.

In another preferred embodiment the linker is a compound comprising two or more repeats of the following formula (III)

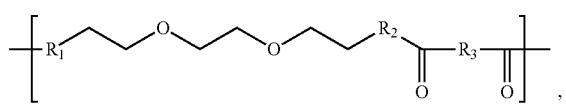

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups.

Preferably, L comprises at least two repeats of the above formula wherein both R1 and $R_2$ are NH and $R_3$ is $CH_2OCH_2$. Preferably, L comprises one or more repeats of the following formula (IV)

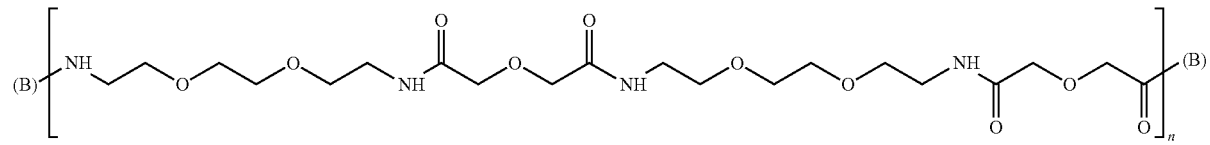

wherein n is an integer from 1 to 10, and (B) is a branching point. The L molecules of this formula and their synthesis are in detail described in WO2007/015168, which is incorporated herein by reference.

By the term "branching point" is meant a point in a polymer molecule wherein a branch, e.g. a side chain of the same polymer, or other molecules may be attached. The branching point may be an atom, a group of atoms, or a functional group via which compounds Y and Z may be directly or indirectly conjugated to L.

There is a great variety of polymer molecules that may be used as linker L. Examples include polysaccharides such as dextrans, carboxy methyl dextran, dextran polyaldehyde, carboxymethyl dextran lactone, and cyclodextrins; pullulans, schizophyllan, scleroglucan, xanthan, gellan, O-ethylamino guaran, chitins and chitosans such as 6-O-carboxymethyl chitin and N-carboxymethyl chitosan; derivatized cellolosics such as carboxymethyl cellulose, carboxymethyl hydroxyethyl cellulose, hydroxyethyl cellulose, 6-amino-6-deoxy cellulose and O-ethylamine cellulose; hydroxylated starch, hydroxypropyl starch, hydroxyethyl starch, carrageenans, alginates, and agarose; synthetic polysaccharides such as ficoll and carboxymethylated ficoll; vinyl polymers including poly(acrylic acid), poly(acryl amides), poly (acrylic esters), poly(2-hydroxy ethyl methacrylate), poly (methyl methacrylate), poly(maleic acid), poly(maleic anhydride), poly(acrylamide), poly(ethyl-co-vinyl acetate), poly (methacrylic acid), poly(vinylalcohol), poly(vinyl alcohol-co-vinyl chloroacetate), aminated poly(vinyl alcohol), and co block polymers thereof; poly ethylene glycol (PEG) or polypropylene glycol or poly(ethylene oxide-co-propylene oxides) containing polymer backbones including linear, comb-shaped or hyperbranched polymers and dendrimers, including branched PAMAM-dendrimers; poly amino acids including polylysines, polyglutamic acid, polyurethanes, poly(ethylene imines), pluriol; proteins including albumins, immunoglobulins, and virus-like proteins (VLP), and polynucleotides, DNA, PNA, LNA, oligonucleotides and oligonucleotide dendrimer constructs; mixed polymers, i.e., polymers comprised of one or more of the preceding examples of polymers, co-block polymers and random co-polymers.

Properties of the chosen polymer can be modified to optimize performance, e.g. the length or branching can be optimized. Furthermore, the polymer may be chemically modified to carry various substituents. The substituents may be further chemically protected and/or activated, allowing the polymer to be derivatized further.

In one preferred embodiment the linker compound between oxidoreductase substrates and labels is a dextran polymer or a conjugate molecule comprising a dextran polymer.

Methods of conjugating polymers with different chemical substances, e.g. labels, are well known in the art and can be used to make conjugates of the invention. For example, the polymer may be activated with vinylsulfon and mixed with a detectable label and a molecule of formula (II) to form the polymer conjugate. In other embodiments, aldehydes can be used to activate a polymer, e.g. dextran, which is then mixed with a detectable label and a molecule of formula (II). Yet another method of preparing polymeric conjugates is by using so called chemo selective coupling schemes for coupling the components together, e.g. molecules can be derivatized with thiol reactive maleimide groups before being covalent coupled to an thiol modified polymeric backbone. In some other embodiments, a molecule for formula (I) and a detectable label can be attached to the polymer via a linking compound. Examples of this method include the use of homobifunctional linker compounds such as glutaric dialdehyde, hexan di isocyanate, dimethylapimidate, 1,5-difluoro-2,4-dinitrobenzene, heterobifunctional cross binders like e.g. N-gamma-maleimidobytyroloxy succinimide ester. Alternatively, chemical substances may be directly conjugated to polymers.

Methods of derivatization of polymers comprising one or more repeats of formula (III) (termed hereafter "L30") are described in detail in WO2007015168, which is incorporated herein by reference.

Exemplary conjugates comprising linkers that are polymers comprising various number of repeats of formula (III), such as a polymer comprising two L30 repeats, (termed L60), such as a polymer comprising three L30 repeats (termed L90), such as a polymer comprising five L30 repeats (termed L150) are described in EXAMPLES.

The amount of the second substrate in the aqueous media (ii) may vary from about $10^{-10}$ M to about $10^{-4}$ M, for example, in case a conjugate (as any of the described above) comprises a radioactive label, the applicable amount may be from about $10^{-10}$ M to about $10^{-6}$ M, and from about $10^{-9}$ M to about $10^{-4}$ M, in case a conjugate comprises a fluorescent label or a label which is a member of a specific binding pair.

Second substrate molecules suitable for the present invention are exemplified in EXAMPLES herein and described in WO2011047680.

For the purposes of the present invention, i.e. to produce deposits of a second substrate under conditions of the invention that are optically appears as distinct dots of stain of a diameter larger than 0.4 micrometer, e.g. around 1 micrometer, 1.5 micrometers, 2 micrometer, 3 micrometer or 4 micrometer, the amount of a first substrate in the aqueous media (A) may vary from around 0.05 mM to around 15 mM, depending on the structure of the compound representing the first substrate.

For example, the amount of a ferulic acid or a derivative thereof as the first substrate in the aqueous media (A) may vary between 0.5 mM and 5 mM, such as for example, around 0.5 mM, around 1 mM, around 1.5 mM, around 2 mM, around 2.5 mM, around 3 mM. The term "around" means a deviation of 1-25% from the indicated value.

Derivatives of hydroxycinnamic acid, such as Alpha-cyano-4-hydroxycinnamic acid, as the first substrate are preferably used in the range from about 1.5 mM to about 15 mM, e.g around 1.5 mM, around 1.75 mM, around 2 mM, around 2.5 mM, around 3 mM, between 3 mM and 4 mM, between 4 mM and 5 mM, between 5 mM and 6 mM, between 6 mM and 7 mM, between 7 and 8 mM, between 8 mM and 9 mM, between 9 and 10 mM, between 10 mM and 11 mM, between 11 mM and 12 mM, between 12 mM and 13 mM, between 13 mM and 14 mM, between 14 mM and 15 mM (including both end points of all mentioned intervals and all values within).

When DAB is used as the first substrate, its amount in an aqueous solution (A) is preferably less than 1 mM, preferably within the range of 0.05 mM to 1 mM, such as between 0.05 mM and 0.08 mM, e.g. around 0.07 mM, i.e. from 0.066 mM to 0.074 mM, or between 0.08 mM to 0.1. mM, e.g. around 0.09 mM, or between 0.1. mM and 0.3 mM, e.g. around 0.15 mM, around 0.2 mM, around 0.25 mM, or between 0.3 mM and 0.6 mM, e.g. around 0.35 mM, around 0.4 mM, around 0.45 mM, around 0.5 mM, around 0.55 mM, or between 0.6 mM and 1 mM, e.g. around 0.7 mM, around 0.75 mM, around 0.8 mM, between 0.8 mM and 1 mM.

During visualization procedure the sample is incubated in different media (e.g. incubation (a), incubation (b)). Non-limiting embodiments of incubation media are discussed below.

Time for maintaining/incubating the sample in the incubation medium may vary depending on the technical effect which is desired to be achieved following the incubation. In different embodiments an incubation may lasts from approximately 3 seconds to approximately 3 min, e.g. around 10 seconds, 20 seconds, 30 seconds, 1 minute, 2 minutes, 5 minutes, 10 minutes. or longer, e.g. one-two hours, overnight. In one embodiment, incubating time at all steps of the method may have the same duration, i.e. every incubating may lasts 5 to 10 minutes, etc. In another sample in an aqueous solution comprising a binding agent (termed hereafter "binding agent solution/media") may lasts 1-3 minutes, incubating in an aqueous media (i) and/or aqueous solution (ii) media may lasts 10 minutes.

Incubating may be performed at various temperatures, depending on the type of target, binding agent, etc. The procedures according to the invention are substantially temperature independent and can be performed at a temperature from around +4° C. to around +40° C., however, if desired, the temperature may be used for extending or reducing duration of an incubation, e.g. lower temperatures may be used to prolong the incubating time, and, vice versa, higher temperatures may be used to shorten the time for incubating.

Basically, binding agent media suitable for the purposes of the invention is a buffered aqueous solution of one or more binding agents that has pH in the range from 4 to 9. In some embodiments the binding agent media may comprise an organic or inorganic salt. The inorganic salt may be selected form e.g. sodium chloride, magnesium chloride, potassium chloride, calcium chloride, sodium phosphate, or ammonium sulfate. The organic salt may be selected from e.g. sodium acetate, ammonium acetate or imidazole salts, e.g. imidazole hydrochloride, etc.

The amount of salt in binding agent media may range from approximately $10^{-3}$ M to saturation, e.g. from approximately 20 mM to approximately 200 mM, or from approximately 50 mM to approximately 500 mM. In one preferred embodiment, the media may comprise salt in the amount from approximately 10 mM to 500 mM. In another preferred embodiment the medium may be free of salt.

As mentioned, typically, the pH value of binding agent media may vary from about 4 to about 9, such as between pH 3.5 and pH 9.5, e.g. between pH 5 and pH 7, between pH 5.5 and pH 6.5 or between pH 6.5 and 7.5, or between pH 7 and pH 8, or between pH 7.5 and pH 8.5, or pH 8 and pH 9. Any buffer with a suitable buffer capacity may be used, e.g. phosphate buffered saline (PBS) and imidazole buffer. Other suitable buffers may be found in Good, Nebr., et al (1966) Hydrogen ion buffers for biological research. Biochem. 5(2), 467-477. The pH value of the media may be essential for binding of binding agent to the target; it may be optimized depending on the nature of the binding agent and the target.

In some embodiments binding agent media may comprise an organic modifier (by the term "organic modifier" is meant any non water solvent), e.g. N-Methyl pyrolidone (NMP), dimethylsulphoxide (DMSO), mono- and diethylene glycol, sulpholane, N,N-dimethylformamide (DMF), polyethylene glycol (PEG), propylene glycol, etc. The amount of the organic modifier may vary from around 1% to around 20% (v/v or w/v), or, in some embodiments, be higher than 20%.

In some embodiments binding agent media may comprise a detergent, e.g. polyethylenglycol-p-isooctyphenyl ether (NP-40)) or a surfactant (e.g. selected from the surfactants based on polyoxyethylene sorbitanmonolaurate (Tween), or a surfactant based on block copolymers (pluronic etc.), etc. The amount of the detergent may vary from about 0.001% to about 5%/v/v or w/v).

In some embodiments binding agent media may comprise a binding agent stabilizing agent, e.g. bovine serum albumin or dextran. The amount of the stabilizing agent may vary from 0.01% to 20% (w/v).

In some embodiments binding agent media may comprise an ion chelator (e.g. ethylene diamine tetra acetic acid (EDTA) or ethylene diamine hydroxyl phenylacetic acid type chelator (EDHPA), etc.). The amount of the chelator may vary from about $10^{-9}$ M to about $10^{-6}$ M.

In some embodiments, binding agent media may comprise one or more blocking agents for saturating non-specific binding sites, i.e. sites of the solid support that do not comprise the target. Some non-limiting examples of blocking agents suitable for different embodiments may be the Denhard's solution, bovine serum albumin, skimmed milk, etc.

As discussed above, the invention contemplates a great variety of species of targets, binding agents and assay formats, accordingly, composition of the binding agent medium may vary and should be adjusted for every particular embodiment using the knowledge of the art.

Amounts of a binding agent in binding agent media may vary depending on the species of the biding agent, sample, target, composition of the media, etc. For example, in one embodiment, when a sample comprise a target that present in a low concentration range, it may be preferred to use relatively high amounts of binding agents in a binding agent media which composition (e.g. pH, salt concentration, etc) and incubation conditions (e.g. duration of incubation with the sample, temperature) are optimized to facilitate interaction between the binding agents and the target (or other binding partners). Optimization of binding between partners of specific binding pairs is a routine procedure for most of binding agents used for the purposes of the invention, so that a skilled in the art can do it by following guidelines of the art. Such optimization sometimes is necessary to secure binding of a binding agent to the maximal possible number of single units of the target or to another binding agent (e.g. a binding agent bound to the target) in the sample.

In one preferred embodiment, the quantity of a binding agent in the binding media may be adjusted to bind all or a fractional sub-population of single target units present in the sample. In another embodiment, a quantity of binding agent is adjusted to bind all or a fractional sub-population of complexes of single target units with another binding agent of the sample. In one embodiment, the fractional sub-population corresponds to a majority of single target units of the sample. In another embodiment, the fractional sub-population corresponds to a minority single target units of the sample. In such embodiments, the composition of binding agent media, e.g. pH, salt content, etc., or incubating conditions, such as temperature, duration etc, may be adjusted so that the affinity of the binding agent to its partner in the sample will be diminished or enhanced and the binding agent will therefore form the binding complexes with a larger or smaller fractional subpopulation of single units of the target present in the sample. In one preferred embodiment, the amount of a binding agent that is capable of specifically binding to its partner in the sample, e.g. a first binding agent, second binding agent and/or amount of binding molecules in a first or second binding agent mixture (see below), is relatively high to saturate all available binding sites in the sample even in conditions that do not favor the partner binding.

The term "fractional subpopulation" in the present context means a portion of the total population of the binding agent partner units in the sample that is equal or less than 99.9%, e.g. equal or less than 99%, 98%, 97% etc, e.g. 75-80%, less than 75%, less than 60%, etc, for example from 1% to 50%, such as from 1% to 25%, etc. In some embodiments the fractional subpopulation may be less than 1% of the total quantity of units of the binding agent partner present in the sample.

In some preferred embodiments, a detectable fractional sub-population of a binding partner of a binging agent in the sample may be predetermined. This may be done by using a mixture of binding molecules of the binding agent, wherein the binding molecules of the mixture are all of the same species and have essentially the same affinity to the (common for all said binding molecules) binding partner in the sample ("essentially" in the present context means that +/−10% difference in the affinity is included), and wherein a portion of said binding molecules is detectably labeled and a portion of said binding molecules is unlabeled, and the both portions are predetermined. The term "labeled binding molecules" means that said binding molecules are associated/linked to a detectable label, e.g. a fluorescent label or enzyme. In one preferred embodiment, the label is an enzyme; in one preferred embodiment the enzyme is an oxidoreductase enzyme, (such as a described above, e.g. HRP). The unlabelled binding molecules do not comprise any detectable label.

In one such embodiment, the binding agent may be a first binding agent that is capable of binding to a single unit of the target and form a complex with said single unit. In another such embodiment, the binding agent may be a second binding agent that has affinity to the first binding agent bound to single target unit in the sample. In some embodiments, the binding agent may be a third binding agent that is capable of binding to the second binding agent, or to a label linked to the second binding agent, or to a reporter deposit at a target site.

Using the binding agent (as any of the mentioned) comprising a predefined ration of labeled and unlabeled binding molecules, it is possible to quantify the amount of a target in the sample precisely by quantifying the target sites (visualized as dots) formed with the labeled binding agent. Methods of quantification of the target in histological samples using mixtures of labeled and unlabelled binding molecules are described in detail in EXAMPLES.

Following the incubation in a binding agent medium, the sample is incubated in an aqueous solution (A) (also termed herein as "reporter deposition media") comprising a first substrate of the enzyme with oxidoreductase activity and, a second substrate of the enzyme with oxidoreductase activity and a peroxide compound.

Optionally, before the incubation in the aqueous solution (A), the sample may be incubated in an aqueous solution (B), which composition is as of an aqueous solution (A) without the second substrate.

Accordingly, in one embodiment the invention relates to incubation media which is in an aqueous solution (A) and in another embodiment the invention relates to incubation media which is an aqueous solution (B).

Both aqueous solution (A) and aqueous solution (B) may be an aqueous buffered solution with a suitable buffer capacity, e.g. phosphate buffered saline (PBS) and imidazole buffer. Other suitable buffers may be found in Good, Nebr., et al (1966) Hydrogen ion buffers for biological research. Biochem. 5(2), 467-477. The pH value of the solutions may be adjusted in order to achieve the technical effect of the incubation, namely formation of discrete deposits of the second substrate of an enzyme with oxidoreductase activity at discrete single target sites of the invention, for example adjusted to pH ranging from about 4 to about 9. However, pH of the aqueous solutions (A) and (B) is of minor importance for the technical effect of the incubation.

Both aqueous solution (A) and aqueous solution (B) may further comprise an organic or inorganic salt.

The inorganic salt may be selected form e.g. sodium chloride, magnesium chloride, potassium chloride, calcium chloride, sodium phosphate, or ammonium sulfate, etc.

The organic salt may be selected form e.g. sodium acetate, ammonium acetate or imidazole salts, e.g. imidazole hydrochloride, etc.

The amount of salt in an aqueous solution (A) and aqueous solution (B) may range from approximately $10^{-3}$ M to saturation, e.g. from approximately 20 mM to approximately 200 mM, or from approximately 50 mM to approximately 500 mM. In one preferred embodiment, the media may comprise salt in the amount from approximately 10 mM to 500 mM. In another preferred embodiment the medium may be free of salt.

Both aqueous solutions (A) and aqueous solutions (B) may in different embodiments further comprise:
(i) an organic modifier and/or
(ii) an enzyme enhancer, and/or
(iii) an iron chelator, and/or
(iv) a detergent, and/or
(v) an anti-microbial agent The organic modifier may be present in the media in the amount from around 1% to around 20% (v/v or w/v), however, in some embodiments higher concentrations of the organic modifier may be required. The organic modifier may for example be polyethylene glycol (PEG). Other examples include but not limited to organic modifiers selected from the group essentially consisting of C1-C4, i.e. lower, alcohols, N-Methyl pyrolidone (NMP), dimethylsulphoxide (DMSO), mono- and diethylene glycol, sulpholane, N,N-dimethylformamide (DMF). In some embodiments it may be advantageous to use polyethylene glycol (PEG), e.g. PEG2000, or propylene glycol. The amount of polyethylene glycol in the media in these cases may vary from about 0.1%

(v/v) to about 20% (v/v), for example from about 1% (v/v) to about 15%, such as 5-10% (v/v).

By the term "enzyme enhancer" is meant any compound which enhances the catalytic activity of peroxidase. Such enzyme enhancer may be selected from the group essentially consisting of phenylboronic acid derivatives and divalent metal ions such as nickel or calcium. The amount of the enzyme enhancer may vary from about $10^{-7}$ to about $10^{-3}$ M.

The iron chelator may be ethylene diamine tetra acetic acid (EDTA) or ethylene diamine hydroxyl phenylacetic acid type chelator (EDHPA). Concentration of the iron chelator may vary from about $10^{-6}$ to about $10^{-6}$ M.

The detergent may be selected from polyethylenglycol-p-isooctyphenyl ether (NP-40), a surfactant selected from the surfactants based on polyoxyethylene sorbitanmonolaurate (Tween), or a surfactant based on block copolymers (pluronic etc.). Concentration of the detergent may vary from about 0.001% to about 5%.

Essential components of an aqueous solution (A) are a first substrate of an enzyme with oxidoreductase activity, a second substrate of said enzyme and a peroxide compound. Embodiments of the first substrate and the second substrates are discussed in detail above.

In one preferred embodiment the first substrate may be 3,3"-diaminobenzidine (DAB) or a derivative thereof. In another preferred embodiment, the first substrate may be ferulic acid or a derivative thereof. In another embodiment, the first substrate may be alpha-cyano-4-hydroxycinnamic acid.

The amount of the first substrate in an aqueous solution (A) may vary depending on the compound chosen as the first substrate (see discussion above). For example, in embodiments, when DAB is chosen as the first substrate, the amount of DAB in an aqueous solution (A) and in aqueous solution (B) is less than 1.4 mM, preferable less than 1.2 mM, preferably less than 1 mM, such as from around 0.005 mM to around 0.5 mM, for example around 0.3 mM, or around 0.2 mM, such as around 0.15 mM, etc. In embodiments when ferulic acid is used as the first substrate, the amount of said compound is less than 2.5 mM, preferably less than 2 mM, e.g. around 1.5. mM. The term "around" in the present context means+/−0.05-0.5 mM.

Amounts of the other first substrates of the invention in the aqueous solutions (A) or (B) are discussed in the previous sections.

The aqueous solution (i) may comprise various amounts of the second substrate of the enzyme, such as from about $10^{-10}$ M to about $10^4$ M. For example, in embodiments when the second substrate (as any of the described above) comprises a radioactive label, an applicable amount may be in the range from about $10^{-10}$ M to about $10^{-6}$ M. In other embodiments, e.g. when the second substrate comprises a fluorescent label or a label which is a member of a specific binding pair, the amount may be in the range from about $10^{-9}$ M to about $10^{-4}$ M.

In one embodiment, an aqueous solution (A) may comprise a population of identical conjugate molecules of second substrate. In another embodiment, an aqueous solution (i) may comprise a population of different conjugate molecules of second substrate.

A preferred peroxide compound of the invention is hydrogen peroxide, however, other peroxide compounds may also be used in different embodiment, e.g. in some embodiments it may be preferred an organic peroxide such as e.g. tert-butyl peroxide, ditert-butyl peroxide, peracetic acid, etc. or in some embodiments it may be an adduct of hydrogen peroxide, such as hydrogen peroxide urea adduct.

The amount of a peroxide compound in an aqueous solution (i) and an aqueous solution (ii) may not be higher than 5 mM, preferably less than 5 mM, preferably in the range of 0.1 mM to 5 mM, e.g. between 0.1 mM and 1 mM, between 1 mM and 2 mM, between 2 mM and 3 mM, or between 3 mM and 4 mM, preferably in the range between from around 1 mM to around 2 mM, such as around 1.5 mM. The term "around" in the present context means+/−0.05-0.5 mM An aqueous solution (A) comprising a first substrate of enzyme with oxidoreductase activity, a second substrate of said enzyme and a peroxide compound is termed herein "deposition medium".

An aqueous solution (B) may comprise the same compounds in the same amounts as an aqueous solution (A), with the exception that the aqueous solution (ii) does not comprise the second substrate of enzyme with oxidoreductase activity.

In some embodiment a sample comprising single target sites may be initially incubated in an aqueous solution (B) and sequentially in an aqueous media (A).

In another embodiment a sample comprising single target sites is incubated an aqueous solution (A), without preincubation in an aqueous solution (B).

According to the invention the deposition media is a stable solution, i.e. no precipitation of the solved compounds occurs for a relatively long period of times, such as at least 5 hours. To prolong the shelf-life of the media it may be useful to store the media at temperatures below +20° C., e.g. at +4-+10° C., and/or to add to the media an anti-microbial compound. The anti-microbial compound may be any antimicrobial compound commonly used for such purpose, e.g. sodium azid, Proclin™ or Bronidox®.

In one embodiment the invention relates to visualization of discrete single deposits of the second substrate at single target sites, e.g. a sample comprising discrete deposits of the second substrate may be incubated further in incubation media comprising a binding agent capable of specifically binding to a detectable label of the deposited molecules of second substrate.

An incubation medium comprising a binding agent capable of specifically binding to a detectable label of the deposited molecules of second substrate will typically have a similar or the same composition as the binding agent medium discussed above.

The binding agent bound to a detectable label of the deposited second substrate may in one embodiment comprise an enzyme, e.g. horse radish peroxidase (HRP) or alkaline phosphotase (AP). Such binding agent can be detected using a standard visualization system employing chromogenic substrates of the enzymes, e.g. an enzyme substrate solution or a color developing solution. This kind of media may be any suitable media known in the art which is to be selected depending on available means for visualization and following the common general knowledge of the art concerning the nature of the detectable label of the deposits. Both HRP and AP generated conventional stains of the deposits may be produced using procedures well known in the art (see e.g. Immunochemical staining methods. Handbook. $3^{rd}$ ed, Dako, 2010). In one embodiment, the stains are produced using by methods described in WO2009036760, WO2010094283 or WO2010094284 (all embodiments of staining procedures disclosed in the latter documents are incorporated herein by reference).

Alternatively, in case the deposit binding agent comprises HRP, the visualization method of the invention may comprise a further step of incubation of a sample comprising discrete deposits of the second substrate bound to said binding agent in the deposition media described above. Such further step may be advantageous in some embodiments when a signal associated with the deposited second substrate may weak, or the size of the primary deposit is relatively small. The additional deposition step allows further amplification of the signal associated with the deposit and it may also increase the size of detectable deposits at single target sites. Further, the step also allows modifying the character of the detectable signal, e.g. changing spectral characteristics of the signal, e.g. the initial label detectable as a red signal may be substituted for a label detectable as a green signal by using conjugate molecules comprising said green label for this additional deposition instead of conjugate molecules comprising a red label used for the initial deposition (at step (b) of the method). Such flexibility of the method of the invention, however do not add an extra complexity to reagents used in additional steps of detection, as all embodiments of incubation media of steps (a) and (b) (discussed above) of the method may be successfully used without substantial modifications in these addition steps.

In one embodiment the invention relates to washing media, i.e. media for removing the rests of compounds (of incubation medium) from the sample after the technical effect of the incubation has taken place. The method of the invention may comprise one or more washing steps typically following a step of incubation of the sample in media described above, e.g. between steps (a) and (b), etc. Typically, a washing medium will be the same medium that has been used for incubating of the sample in a step preceding the washing step without the essential compounds of the incubation media, i.e. without binding agent, substrates of the enzyme, etc.

In one embodiment, the invention relates to a media for quenching the endogenous oxidoreductase activity. This type of media may be any media of such kind that is routinely used for the purpose in the art, for example a solution of hydrogen peroxide. This medium may be used before step (a) of the method. It can also be used after step (b) and before additional steps of detection of the deposited second substrate. Application of this medium at this stage of the procedure may used for quenching the residual oxidoreductase activity in the sample.

The above described method of producing distinct dots of enzymatically deposited stain is not limiting the invention. Other methods that utilize affinity binding agents for detection of target units at single target sites and an enzyme-mediated deposition of a stain at this target sites that dot staining are also included in the scope of the invention.

Thus, in one embodiment, a target dot staining of the methods of the invention may be produced by a method that combines the rolling circle amplification (RCA) of a signal associated with a single target site and enzymatic deposition of a stain at that target site. Such methods are well-known in the art (see e.g. Söderberg, O. et al., Direct observation of individual endogenous protein complexes in situ by proximity ligation, *Nat. Methods* 3, 995-1000 (2006); Tao, R.-H. & Maruyama, I. N., EGF(ErbB) receptors have preformed homo- and heterodimeric structures in living cells J. Cell Sci. 121, 3207-3217 2008; or Mats Gullberg & Ann-Catrin Andersson, Highly specific detection of phosphorylated proteins by Duolink, *Nature Methods* 6, (2009)) and reagents are available from Olink Bioscience.

3.4.2. Staining with Second Stain

Staining a target in the sample with a second stain according to the invention, in one embodiment, may be done using a traditional/conventional method for IHC staining, e.g. the HRP-mediated deposition of a HRP detectable substrate such as DAB, or AP-mediated deposition of an AP detectable substrate such as Liquid Red (LR) stain.

By the term "traditional/conventional conventional method for IHC staining" in the present context is meant a method comprising, generally: (i) a step of detection of the target in the sample with a binding agent that is a member of a specific binding pair with the target, (ii) a step of direct or indirect labeling the target with an enzymatic activity, such as horseradish peroxidase or alkaline phosphatase activity, and (iii) labeling the sites comprising target and enzymatic activity with a stain which is a substrate of the target associated enzyme, wherein the stain is deposited at target sites and appears to the microscopist as a homogeneous color pattern marking the sites of the sample comprising target with intracellular resolution of cellular structures, e.g. membrane, cytoplasm, and nucleus, and without distinguishing individual single units of the target. These methods are well known in the art (see e.g. Immunochemical staining methods. Handbook. $3^{rd}$ ed, Dako, 2010).

Binding agents describes herein may be used for the purposes of both staining with the first and second stain (staining (a) and (b) correspondingly).

Both visualization of target sites with staining (a) and (b) may employ binding agents labeled with HRP activity, wherein the binding agents have different binding affinity partners in the sample: in staining (a) the binding agents that recognize and bind to deposits of the second substrate, and in staining (b) the binding agents that recognize and bind the target. Due to difference in appearance of the stainings (a) and (b), the same detectable substrate to mark the target sites of one (the same target) or more (different targets) may be used. In one embodiment, binding agents for recognition of the deposits of second substrate of staining (a) and binding agents for recognition of the target of staining (b) may labeled with different enzymes, e.g. binding agents (a) with HRP and binding agents (b) with AP, or vice versa.

In one embodiment, the stains may be produced using a method described in WO2009036760, WO2010094283 or WO2010094284 (all embodiments of staining procedures disclosed in the latter documents are incorporated herein by reference).

The methods described in the above documents and of the present invention use a target site directed HRP-mediated (or another oxidoreductase enzyme-mediated) deposition of a detectable substrate. Both binding agents and the enzyme substrates are similar or the same as the described above for visualization of single target sites as distinct dots. However, the methods provide a staining pattern that is similar with the uniform staining pattern of a routine HRP-DAB immunostaining, but not with the dot staining described herein. The difference in staining pattern is secured by performing deposition of a second enzyme substrate (i.e. reporter) in deposition media that has different composition for staining (a) and staining (b) and use an amount of binding agent(s) to recognize target unit in the sample and mark the target sites with the enzyme activity that is higher in staining (b) than in staining (a).

In particular, visualization of target sites in a histological sample, in one embodiment, comprises,
  a) incubating the sample comprising a population of individual units of a target with of one or more binding agents, wherein (1) at least one of the binding agents comprises an enzyme with oxidoreductase activity;
(2) at least one of the binding agents is capable of directly binding to an individual single unit of the target,
and forming one or more discrete single target sites a fractional sub-population of individual single units of the target, wherein each single discrete single target site comprises a complex of one individual single unit of said fractional sub-population and one or more binding agents, at least one thereof comprising the enzyme;
c) incubating a sample of (a) in an aqueous solution (A) comprising
a peroxide compound in an amount that is more than 2 mM, preferably around or more than 5 mM;
a first substrate of the enzyme associated with discrete single target sites of (a) and,
a second substrate of said enzyme,
wherein said first substrate is a water soluble electron rich organic compound which is
(3) capable of generating a radical upon a reaction with said enzyme; and
(4) capable of cross-linking molecules of said second substrate in the presence of both said enzyme and a peroxide compound, thereby producing a water insoluble polymeric product of said second substrate,
and wherein said second substrate is a conjugate molecule comprising at least two compounds that are capable of serving as substrates of said enzyme and a detectable label, wherein the detectable label is selected from the group consisting of a fluorescent, luminescent, radioactive or chromogenic matter and a member of a specific binding pair,
thereby forming discrete deposits of the second substrate at discrete single target sites of (a) and visualizing said single target sites of (a) as a uniform staining pattern optically observable as a homogenous stain.

A fractional sub-population of individual target units in one preferred embodiment is the residual individual target units that are not visualized in staining (a). In one embodiment, the fractional sub-population may be around 5-10% of the all target units in the sample, or more, e.g. around 10-20% or more, around 15-30% or more, around 25-35% or more, etc.

The amounts of the binding agents in the incubation media may be adjusted according to guidelines of the art (discussed above).

To produce deposits of a second substrate of the invention that optically appears as a uniform staining pattern observable as a homogenous stain and not as distinct dots of stain of a diameter larger than 0.4 micrometer, the deposition media (i.e. aqueous solution A) should contain certain amounts a peroxide compound and a first substrate of the enzyme associated with the target sites.

The peroxide compound may be selected from organic peroxides such as tert-butyl peroxide, ditert-butyl peroxide, peracetic acid, or it may be an adduct of hydrogen peroxide, such as hydrogen peroxide urea adduct. In some embodiments hydrogen peroxide ($H_2O_2$) is a preferred peroxide compound. The amount of $H_2O_2$ in the media may vary from 1.5 mM to 150 mM in different embodiments, e.g. from about 6 mM to about 100 mM, from about 5 mM to about 50 mM, from about 10 mM to about 15 mM, etc.

In one preferred embodiment the amount of $H_2O_2$ in the deposition media is more than 5 mM, e.g. from 5.1 mM to 65 mM, such as between 5.2 mM and 55 mM, such as from 5.3 mM to 45 mM, such as between 5.4 mM and 35 mM, such as from 5.5 mM to 25 mM, such as from 5.6 mM to 15 mM.

The amounts of the first substrate, e.g. DAB, in the deposition media may vary depending on the amount of $H_2O_2$ in the media. In some embodiments DAB may present in an amount that is less than 1 mM, e.g. between 0.25 mM and 0.85 mM, with the proviso that the amounts of $H_2O_2$ in this deposition media is higher than 5.5 mM e.g. from 5.6 mM to 56 mM. In other embodiments, DAB may present in the deposition media an amount that is more than 1.5 mM, e.g. between 1.5 mM and 6 mM, wherein the amount of $H_2O_2$ is from 1.5 mM to 159 mM Preferably, the amount of DAB in the deposition media is more than 1.5 mM, e.g. between 1.5 mM and 6 mM. This amount of DAB provides for a very specific and abundant deposition of reporter molecules from the deposition media comprising $H_2O_2$ in c concentration range from 1.5 mM to 159 mM. The amounts of DAB from 3 mM to 6 mM provide for a very specific and abundant deposition of reporter molecules, which ensures both crispness and intensity of the final staining of the reporter deposits, e.g. in immunohistochemical detection. The amounts of DAB ranging from 1.5 mM to 3 mM provide for a slightly more blurry but still strong signal (compared to DAB in an amount from 3 mM to 6 mM), which may be advantageously used in detection of low abundance targets in some embodiments. In such embodiments to enhance saturation of target sites with deposited reporter, the duration of incubation of sample in the deposition media may be prolonged, e.g. to 3-5 min compared to 1 min incubation at higher amounts of DAB. However, as mentioned, the crispness of the final staining of the target will be significantly reduced.

The amount of another suitable first substrate, e.g. alpha-cyano-4-hydroxycinnamic acid, in the deposition media may vary from 3 mM to 10 mM, such as round 4 mM, around 5 mM, around 6 mM etc., and the amount of $H_2O_2$ may be in the range between 1.5 mM and 6 mM, such from around 2 mM to around 4 mM, e.g. around 3 mM. The staining in such conditions is crisp and intense (reflecting the target precise and effective deposition of a reporter).

In one embodiment, detectable enzyme substrates visualizing the target sites used on step (a) and step (b) are different chromogenic substances. A number of different chromogenic substrates of enzymes, e.g. HRP or AP, is adopted for IHC staining, and may be suitable for carrying out the IHC staining of steps (a) and (b) of the present method. Exemplary substances are described in Examples. Other suitable substances are described in WO2011047680, WO2009036760, WO2010094283, WO2010094284 or PCT/DK2011/000131 (these embodiments are incorporated herein by reference).

4. Staining with Histological Stain

Before or after staining with a first IHC stain (staining a) or second IHC stain (staining (b)), the sample may be stained with a histological stain.

By the term "histological stain" is generally meant a stain that has ability to visualize or differentially identify microscopic structures in a histological sample. This term is part of general knowledge in the fields of histology and histopathology and a skilled in the art is familiar with the term and its meaning. Some examples of a histological stain suitable for the purposes of the invention are described in Michael H. Ross, Wojciech Pawlina, (2006). *Histology: A Text and Atlas*. Hagerstown, Md.: Lippincott Williams & Wilkins, or in Education Guide: Special stains and H&E, $2^{nd}$ edition, Kumar G L and Kleman G A eds, Dako, 2010.

In one embodiment, a histological stain is a hematoxylin stain. In another embodiment a histological stain is a combined stain, e.g. a hematoxylin and eosin (H&E) stain. A hematoxylin or H&E staining protocol may include any protocol routinely used in the art.

In one embodiment, a histological stain of step (c) may be a special stain. The selection of a special stain to reveal morphology of a tissue sample depends on the tissue sample under evaluation. A skilled in the art can easily choose the appropriate stain and staining protocol following instructions of the art (e.g Education Guide: Special stains and H&E, 2$^{nd}$ edition, Kumar G L and Kleman G A eds, Dako, 2010).

5. Additional Steps

Methods of the invention may comprises one or more additional steps, e.g. washing steps between staining of step (a), (b) and (c), finishing the staining with mounting the slide with mounting media, etc.

In one embodiment, a tissue sample stained according to step (a) and (c) and, optionally, stained according to step (b), may be further processed analyzing the sample content, e.g. there may be determined the level of expression of one or more stained targets, regional distribution of one or more stained targets, or total amount of one or more targets, etc. It may also be evaluated a relative expression of a target in sample, wherein the target expression may be evaluated relative to another target, e.g. relative to a house-keeping protein, relative to a sample area, to sample volume, to another object present in a sample, e.g. a cellular structure, etc.

Quantification of the target may be done manually or automatically, e.g. according to the methods described in PCT/DK2011/000131 (the methods described therein are incorporated herein by reference), or PCT/US2011/6242 (the methods described therein are incorporated herein by reference) o, or according to any other method developed for quantification of optically detectable target in histological samples developed in the art.

Embodiments of Methods of the Invention

The below are non-limiting embodiments of the visualization procedures according to the present invention. All terms and embodiments that are discussed throughout the text above are applicable to any embodiment described below.

1. Visualization of One Target

In one embodiment, the invention relates to a method (I) of visualization of a target in a histological sample, comprising in any order:
 a) staining the sample with a first stain,
 b) staining the sample with a second stain,
 c) staining the sample with a third stain,
 wherein
 (i) the first stain and the second stain are generated via an enzyme mediated deposition of a detectable enzyme substrate at sites of the sample comprising the target;
 (ii) the first stain visualizes a first fractional sub-population of target units, and the second stain visualizes a second fractional sub-population of target units;
 (iii) the first stain and second stain are optically distinguishable by their staining patterns, wherein the staining pattern of the first stain is characterized in that it consists of distinct dots; and
 (iv) the third stain is a histological stain that visualize morphological features of the tissue sample.

In one preferred embodiment of method (I), staining (b) is a conventional IHC staining providing a uniform staining pattern of homogenous color.

In one embodiment of method (I), a conventional staining of step b may precede the dot staining of step a, and the enzyme activities associated with target units of the first fractional sub-population on step (a) and with target units of the second fractional sub-population on step (b) may be different enzymatic activities (e.g. HRP on step (a) and AP on step (b)). The visualization procedure may be performed as the following (method (I) A):
 i) Marking a minor sub-population of the target sites with HRP activity;
 ii) Marking the residual (or a major sub-population) of the target sites with AP activity;
 iii) Depositing an AP substrate at sites (ii) and thereby visualizing said sites;
 iv) Depositing an HRP substrate at sites (i) and thereby visualizing said sites.

In another embodiment, the conventional staining (step b) may precede the dot staining (step a) and enzyme activity associated with the target sites (a) and target sites (b) may be the same, namely an oxidoreductase activity, e.g. HRP. Target visualization may performed as the following (Method (I) B):
 i) Marking a first sub-population of the target with HRP activity;
 ii) Depositing a first HRP substrate and visualizing the first sub-population of target units as uniform staining pattern;
 iii) Marking a second sub-population of the target with HRP activity;
 iv) Depositing a second HRP substrate and visualizing the second sub-population of target units as distinct dots.

In another embodiment, the conventional staining (step b) may precede the dot staining (step a), the enzyme activities associated with target units on step (a) and with target units on step (b) may be either different enzymatic activities (e.g. HRP on step (a) and AP on step (b)) or the same, i.e. an oxidoreductase activity, e.g. HRP activity. Target visualization is performed as the following (Method (I) C):
 i) Saturating the target sites in the sample with a mixture comprising different molecules of one target specific binding agent, wherein a first portion of the binding agent molecules comprises HRP or AP and a second portion of the binding agent molecules comprises a detectable label which is not HRP (e.g. a hapten);
 ii) Visualizing target sites saturated with the first portion of binding agent molecules as uniform staining pattern by depositing a first stain at said target sites;
 iii) Detecting in the sample the target sites saturated with a second portion of target molecules and marking said target sites with HRP activity;
 iv) Visualizing target sites (iii) as distinct dots by depositing a substrate of HRP at said target sites.

In one embodiment, the conventional staining (step (b)) may follow the dot staining (step (a)) (Method (I) D). In this embodiment, visualization procedures may be performed as the following:
 i) Marking a first fractional sub-population of target sites with HRP activity;
 ii) Visualizing the first fractional sub-population of the target sites as distinct dots by depositing a first stain at said sites, wherein the stain is a substrate of HRP;
 iii) Marking a second fractional sub-population of the target sites with HRP or AP activity;

iv) Visualizing the second fractional sub-population of the target sites as uniform staining pattern by depositing a second stain at said sites, wherein the stain is a substrate of HRP or AP.

Any of the above embodiments of method (I) may be preferred. In one preferred embodiment, the invention relates to visualization of a target according to method (I) D.

In another embodiment, the invention relates to a method (II) for visualization of a target in a histological sample, comprising in any order:
  a) staining the sample with a first stain,
  b) staining the sample with a second stain,
  c) staining the sample with a third stain,
  wherein
  (i) the first stain and the second stain are generated via an enzyme mediated deposition of a detectable enzyme substrate at sites of the sample comprising the target;
  (ii) the first stain visualizes a first fractional sub-population of target units, and the second stain visualizes a second fractional sub-population of target units;
  (iii) the first stain and the second stain have the same staining pattern, wherein the staining pattern is characterized in that it consists of distinct dots;
  (iv) the first stain and second stain are distinguishable from each other by their optical features, preferably by color,
  and
  (v) the third stain is a histological stain that visualize morphological features of the tissue sample.

Thus, according to the invention, two or more different fractional sub-populations of the same target may be visualized using a staining procedure that provides the dotted pattern. To distinguish the different fractional sub-populations of target units in the stained sample, different detectable enzyme substrates generating different colors may be used for deposition at target sites corresponding to the different fractional sub-populations of target units.

In one embodiment, the first fractional sub-population of the target is a minor portion of the total amount of the target in the sample, and the second fractional sub-population of the target is a major portion of the total amount of the target in the sample. In one embodiment, the first and the second fractional sub-populations may be especially of the same size, i.e. comprise essentially the same number of target units ("essentially" means around 25% more or less).

In one embodiment, the first stain differs from the second stain by optical features, e.g. color, e.g. the first stain may be red and second stain may be brown, etc.

The staining (a) and (b) in a preferred embodiment employs target specific binding agents to link the target to the enzymatic activity. In a preferred embodiment, at least one target specific binding agent of staining (a) and at least one target specific binding agent of binding (b) is a member of a specific binding pair with the target.

In one embodiment, at least one target specific binding agent of staining (a) and at least one target specific binding agent of staining (b) may be the same binding molecule. In another embodiment, at least one target specific binding agent of staining (a) and at least one target specific binding agent staining (b) are different binding molecules.

In one preferred embodiment, at least one specific binding agent of staining (a) and at least one specific binding agent of staining (b) is or comprises an antibody, nucleic acid or nucleic acid analog.

In one embodiment, the first and the second stain are generated via deposition of a detectable enzyme substrate mediated by the same enzyme. In one preferred embodiment, the enzyme is Horseradish peroxidase (HRP).

In another embodiment, the first and the second stain are generated via deposition of a detectable enzyme substrate mediated by different enzymes. In one preferred embodiment, the enzyme generating the first stain is Horseradish peroxidase (HRP) and the enzyme generating the second stain is Alkaline phosphatase (AP).

In one embodiment, a distinct dot of the first stain has an apparent visual diameter from around 0.4 micrometers to around 4 micrometers.

In one embodiment, the third stain is hematoxylin. In another embodiment, the third stain a combined histological stain, such as hematoxylin and eosin stain. In another embodiment, the third stain is a special histological stain, such as e.g. a stain selected from
  Acid Fast Stain (for mycobacteria)
  Acid Fast Stain
  Alcian Blue Stain
  Alcian Blue-PAS Stain (PAB)
  Hyaluronidase Digestion for Alcian Blue
  Alizarin Stain for calcium
  Auramine-Rhodamine Stain (fluorescent)
  Bielschowsky Stain (for senile plaques)
  Bile Stain
  Bodian's Stain
  Colloidal Iron Stain
  Congo Red Stain
  Copper Stain
  Elastic van Gieson Stain
  Elastic—Weigert's resorcin-fuchsin method
  Modified Elastic van Gieson Stain
  Fontana-Masson Stain for melanin
  Melanin Bleach
  Fraser Lendrum Stain
  Giemsa (Modified May-Gruenwald) Stain (for hematopoietic tissues)
  Giemsa Stain (for Helicobacter)
  Gram (Modified Brown-Brenn) Stain
  Gridley's Stain for ameba
  Grimelius Argyrophil Stain (Pascual's Method)
  Grocott's Methenamine Silver (GMS) Stain
  Holzer's Glial Fiber Stain
  Hortega's Pineal Stain
  Iron Stain (Prussian blue)
  Iron Stain (Turnbull's blue)
  Jones' Silver Stain
  Luxol Fast Blue (LFB) Stain
  Methyl Green Pyronin (MGP) Stain
  Mucicarmine Stain
  Nissl Stain
  Oil Red O Stain
  Orcein Stain
  Periodic acid-Schiff Stain (PAS)
  Periodic acid-Schiff, digested Stain (PAS-D)
  PTAH Stain
  Reticulin Stain
  Spirochete Stain (Steiner & Steiner method)
  Sudan Black B Stain (for lipochrome)
  Sudan Black B Stain (for fat)
  Trichrome Stain—Masson's method
  Trichrome Stain—microwave method
  Thioflavin S Stain (for amyloid in tissues)
  Modified Thioflavin S Stain (for senile plaques)
  Toluidine Blue Stain (for mast cells)
  Urate Crystal Stain
  VonKossa Stain for calcium In one preferred embodiment the target is a biological marker. In one preferred embodiment, the target is a protein or a nucleic acid Some non-limiting working examples of the above embodiments are described in Examples.

2. Visualization Two or More Targets.

In one embodiment, the invention relates to a method for visualization of two or more targets in a histological sample, comprising in any order
  a) staining the sample with a first stain,
  b) staining the sample with a second stain,
  c) staining the sample with a third stain,
  wherein
  (i) the first stain and the second stain are generated via an enzyme mediated deposition of a detectable enzyme substrate at sites of the sample comprising the target;
  (ii) the first stain visualizes target sites comprising units of a first target;
  (iii) the second stain visualizes target sites comprising units of a second target;
  (iv) the first stain and second stain are distinguishable by their staining patterns, wherein the staining pattern of the first stain is characterized in that it consists of distinct dots, and the staining pattern of the second stain is a uniform staining pattern of homogenous color; and
  (v) the third stain is a histological stain that visualize morphological features of the tissue sample and does not visualize the target.

In a preferred embodiment, the first stain differs from the second stain by optical features, e.g. color. e.g. the first stain may be red and second stain may be brown, etc.

The staining (a) and (b) in a preferred embodiment employs target specific binding agents to link the target to the enzymatic activity. In a preferred embodiment, at least one target specific binding agent of staining (a) and at least one target specific binding agent of binding (b) is a member of a specific binding pair with the target.

In one embodiment, at least one target specific binding agent of staining (a) and at least one target specific binding agent of staining (b) may be the same binding molecule. In another embodiment, at least one target specific binding agent of staining (a) and at least one target specific binding agent staining (b) are different binding molecules.

In one preferred embodiment, at least one specific binding agent of staining (a) and at least one specific binding agent of staining (b) is or comprises an antibody, nucleic acid or nucleic acid analog.

In one embodiment, the first and the second stain are generated via deposition of a detectable enzyme substrate mediated by the same enzyme. In one preferred embodiment, the enzyme is Horseradish peroxidase (HRP).

In another embodiment, the first and the second stain are generated via deposition of a detectable enzyme substrate mediated by different enzymes. In one preferred embodiment, the enzyme generating the first stain is Horseradish peroxidase (HRP) and the enzyme generating the second stain is Alkaline phosphatase (AP).

In one embodiment, a distinct dot of the first stain has an apparent visual diameter from around 0.4 micrometers to around 4 micrometers.

In one embodiment, the third stain is hematoxylin. In another embodiment, the third stain a combined histological stain, such as hematoxylin and eosin stain. In another embodiment, the third stain is a special histological stain (some examples of suitable special stains are mentioned above).

In one preferred embodiment the target is a biological marker. In one preferred embodiment, the target is a protein or a nucleic acid In one embodiment, more than two different targets, e.g. three different targets, may be visualized in a histological sample. To visualize the third target, a sample stained according to the method above, may be stained with a fourth stain,
  (i) wherein the fourth stain is generated via the HRP-mediated deposition of a detectable enzyme substrate at sites of the sample comprising the third target;
  (ii) wherein the fourth stain visualizes the third target as distinct dots of fourth stain,
  (iii) wherein the distinct dots of fourth stain have different optical features compared to the distinct dots of first stain.

A preferred different optical feature of dots of the first stain and dots of the fourth stain is color, e.g. dots of the first stain may be red and dot of the fourth stain may be green. The dots may also be different in size or other optical features (examples of optical features of the dots and the methods to program thereof are disclosed in WO2011047680 and PCT/US2011/6242 and incorporated herein by reference).

In one embodiment, the third target is a biological marker which is different the first biological marker.

In one embodiment, the second target is a reference marker. In one embodiment, the second target is a protein or a nucleic acid.

In one preferred embodiment, the histological sample is a sample comprising cells, e.g. a sample of a body tissue or sample of a tumor. In one preferred embodiment, the sample is a solid tissue sample or a cell comprising sample, wherein the cells are immobilized on/into a solid support.

In one embodiment, the invention relates to a method as any of the above, further comprising determining amount of the target in the sample. In one embodiment, the amount of the first target is determined. In another embodiment, the amount of the third target is determined. In one embodiment, the amount is the total amount of the corresponding target in the sample. In another embodiment, the amount is a relative amount of the target, e.g. a relative amount of a first target to a second target and/or to a third target. The methods of the invention allow visualization of multiple targets (two or more) and quantification thereof.

As discussed above, methods of the present invention are especially advantageous for medical diagnostics based on evaluation of histological samples stained with different histological stains in vitro, e.g. for diagnosing a disease in a human or animal subject (termed herein "subject" or "individual"); monitoring a therapeutic treatment in a subject, selecting a therapeutic treatment for a subject, etc. Accordingly, in one embodiment, the invention relates to a method for medical diagnosis, comprising a step of processing a histological sample obtained from an individual (subject) according to a method as any of the discussed above. In particular, the methods are useful for diagnostic of diseases wherein determination of the expression and sub-cellular distribution of one or more biomarkers of the disease is essential for both the correct diagnosis and treatment.

EXAMPLES

The below is a description of non-limiting selected working examples illustrating the invention.

Reagents

If not specified, the used reagents are either purchased from the recognized manufacturers or produced using the procedures described in WO2011047680 or WO2010094283 (the procedures are incorporated herein by reference) or follow the standard procedures of the art, e.g. procedures for solid-phase synthesis, conjugating polymers (including antibodies) with different labels, producing antibodies, antibody manipulation, etc. Exemplary production procedures for two selected compounds are described below.
Goat Anti-Rabbit Antibody Conjugated with Dex70 Conjugated with HRP (L348.111, Fractions 10-11.)

11 nmol 70 kDA MW dextran was reacted with 484 nmol HRP in 316 microliters of buffer A (100 mM NaCl, 25 mM NaHCO$_3$, pH 9.5) for 3 h at 40 C. Thereafter 44 nmol Goat-anti-Rabbit 196 microL water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising Goat-anti-Rabbit (GaR) and HRP. The product was divided into 4 fractions based on conjugate size: The first two fraction containing product (Frac. 8-9) eluded as a first peak, presumably containing some cross linked conjugates, then followed by a broad shoulder that was divided into fractions 10-11 (homogeneous large conjugates) and fractions 12-21 (smaller variable conjugates) and finally unconjugated enzymes and antibodies in fractions 22-42. Measurements on individual product fractions, as well as fractions containing non-conjugated antibody and HRP, showed a total conjugate recovery of 87%. Assuming direct proportionality between incorporated HRP and Dextran showed that fractions 10-11 contained 10.9 HRPs and 0.96 antibodies per Dextran. Only these two fractions were used for experiments.
Preparation of conjugate molecule Goat-anti-Rabbit F(ab)$_1$-(HRP)$_1$ (D 20149) is described in in WO2011047680 (see compound AMM279.168). Conjugate antiFITC-Fa(ab)$_1$-(HRP)$_1$ (D20154) is prepared in the same way substituting AP for HRP.
D21067 Sin-Lys(Sin)-Lys(Sin)-L150-Lys(Flu)

Conjugates labeled with cinnamic acid (Sin) derivatives in solution phase following solid phase synthesis of intermediates carrying free N-terminal amino groups and free lysine side chains amino groups. Alpha-N-Boc-(epsilon-N-2-Cl—Z)-lysine was used to introduce lysine residues giving free epsilon-N-amino groups following cleavage from resin. The solution phase labeling is basically an extension of solid phase techniques, utilizing that the relative high molecular weight intermediates can be almost quantitatively precipitated with diethyl ether from TFA or NMP solution.
Preparation of D210053 (Fer-Lys(Fer)-L150-Lys(Lissamin), D20171 (Fer-Lys(Fer)-Lys(Fer)-Lys(Fer)-L150-Lys(carboxyFluorescein)) is described in WO2011047680.
Other Reagents
Incubation Media (1)

0.1% 4-aminoantipurine, 0.2% Procline 2% BSA, 0.2% Casein, 2% PEG, 0.1% Tween20, 0.1 M NaCL, 10 mM HEPES, pH 7.2. (ABCPT-buffer)
Incubation Media (2):

50 mM imidazole HCl pH 7.5, 0.1% Nonidet P40, 0.1%, benzalkonium chloride, 0.005% (1.5 mM) hydrogen peroxide

EXPERIMENTALS

Experiment 1 Visualization of One Target by Staining (a) in a Histological Sample Stained with Haematoxylin and Eosin (HE Stain)

Slides with formalin fixed paraffin embedded sections of multiple human tissue samples were used as test material.

The slides were deparaffinated in xylene (2×5 min), 99% ethanol (2×2 min) then 70% ethanol. The slides were transferred to water for 5 min, then they were boiled in microwave oven in target retrieval solution for 10 min (Dako low pH, S1699).

Following cooling the slides were transferred to an Autostainer instrument and subjected to the following staining protocol:
Pre rinse with wash buffer (Dako S3006)
Peroxidase blocking solution (Dako S2023), 5 min.
Wash (Dako S3006)
Pan specific anti cytokeratin (Dako M3515) premixed with Goat-anti-Mouse-Dex150-HRP (L348.121), both 20 nM. then diluted to 20 pM, 5 min.
Wash (Dako S3006)
5 microM D21067, 0.28 mM DAB in incubation media 2, for 10 min.
Wash (Dako S3006)
antiFITC-F(ab)$_1$-(AP)$_1$ (D 20036), 20 nM in incubation media 1, 10 min
Wash (Dako S3006)
BCIP/NBT (Dako K5098 Ready To Use), 10 min
Wash (Dako S3006)
Haematoxilin (Dako S3301)
Wash de-ionized water
Wash (Dako S3006)
Wash de-ionized water
99.9% ethanol 1 min
Eosin Y stain, (Steosgal, American MasterTech Scientific), 1 min
99.9% ethanol 1 min
The slides were mounted with permanent mounting media, (Tissue-Tek from Sakura).
Results:

The slides showed the conventional H and E stain, in combination with black dots in tissue expressing cytokeratin. The number of dots corresponded to the expression level of cytokeratin. This allows conventional visual examination of the H and E staining pattern in combination with dot enumeration to assess cytokeratin expression levels.

Experiment 2 Visualization of One Target by Staining (a) and (b) in a Histological Sample Stained with Haematoxylin Slides were pretreated as in experiment 1, and subjected to the following staining protocol on the Autostainer:
Pre rinse with wash buffer (Dako S3006)
Peroxidase blocking solution (Dako S2023), 5 min.
Wash (Dako S3006)
antiHer2 antibody, clone Dak 3-25-11, 6 nM for 20 min.
Wash (Dako S3006)
Goat-anti-Rabbit-Dextran70-HRP, (Lit 348.111, fraction 10-11) in incubation media 1. Varying concentration 12, 6, 3 and 1.5 picoM for 20 min.
5 microM D21067, 0.28 mM DAB in incubation media 2, for 10 min.
Wash (Dako S3006)

antiFITC-F(ab)$_1$-(AP)$_1$, (D20036:), 20 nM in incubation media 1, 10 min
Wash (Dako S3006)
Liquid Permanent Red, (Dako K0640), 10 min
Wash (Dako S3006)
Goat-anti-Rabbit F(ab)$_1$-(HRP)$_1$ (D 20149), 40 nM in incubation media 1, 20 min
Or
Goat-anti-Rabbit F(ab)$_1$-(HRP)$_1$ (D 20149), 40 nM mixed with 40 nM unlabbel Goat-anti-Mouse in incubation media 1, 20 min.
Wash (Dako S3006)
DAB, (Dako K5007), 5 min
Wash (Dako S3006)
Haematoxilin (Dako S3301)
Wash de-ionized water
Wash (Dako S3006)
The slides were mounted with Dako Faramount, (S3025).

Results:

The slides were double stained with co localized red dots and brown DAB deposit in HER2 positive tissue, in tonsil, mamma carcinoma and colon. The number of Dots was proportional to the concentration of Goat-anti Rabbit-Dextran-HRP. The intensity of the brown DAB stain was highest on slides where Goat-anti-Rabbit F(ab)1 was used alone, and between 0.5 and 1 grade lower on slides where the reagent had been mixed with unlabelled Goat-anti-Rabbit. This demonstrates three color combination of conventional IHC (brown), haematoxylin (Blue) and red dots. I.e. a pathologist may examine the conventional brown/blue staining pattern, and use the dots to quantify the HER2 expression level. Concentration of secondary antibodies and/or mixing with unlabelled antibodies, may be used to adjust staining intensity of DAB and number of dots.

Experiment 3 Use of Different Chromogens for Staining (a)

Slides with formalin fixed paraffin embedded sections of HercepTest control cell lines were used as test material.

The slides were deparaffinated in xylene (2×5 min), 99% ethanol (2×2 min) then 70% ethanol. The slides were transferred to water for 5 min, then they were boiled in microwave oven in target retrieval solution for 10 min (Dako pH 9 S2367).

Following cooling the slides were transferred to an Autostainer instrument and subjected to the following staining protocol:
Pre rinse with wash buffer (Dako S3006)
Peroxidase blocking solution (Dako S2023), 5 min.
Wash (Dako S3006)
antiHer2 antibody, clone Dak 3-25-11, 3 nM for 10 min.
Wash (Dako S3006)
Goat-anti-Rabbit-Dextran70-HRP (Lit 348.111, fraction 10-11) in incubation media 1
10 microM D21067, 1.5 mM hydrogen peroxide, 0.14 mM DAB in deposition media 2, for 10 min.
Wash (Dako S3006)
antiFITC-F(ab)$_1$-(AP)$_1$ (D 20036), 20 nM in incubation media 1, 10 min (Slides 1-4)
or
antiFITC-Fa(ab)$_1$-(HRP)$_1$ (D20154), 20 nM in incubation media 1, 10 min (Slides 5-10)
Wash (Dako S3006)
Each slide was then manually stained in the following way:
Slide 1: Liquid Permanent Red, (Dako K0640), 10 min.
Slide 2: Fuchsin+, (Dako K0625), 10 min.
Slide 3: BCIP/NBT, (Dako K0598), 10 min
Slide 4: BCIP/NBT, (Dako K0598), 2×10 min
Slide 5: DAB (Dako K5007), 10 min
Slide 6: D21053 (Fer-Lys(Fer)-L150-Lys(Lissamin)), 400 microgram/mL in DAB substrate buffer from Dako 5007, 10 min
Slide 7: D20171 (Fer-Lys(Fer)-Lys(Fer)-Lys(Fer)-L150-Lys (carboxyFluorescein)), 1 mg/mL in DAB substrate buffer from Dako 5007, 10 min
Slide 8: Blue chromogen 1 mg/mL in DAB substrate buffer from Dako 5007, 10 min
Slide 9: AEC+, (Dako K3461), 10 min
Slide 10: NovaRed, (SK-4800, Vector Laboratories), 10 min
The slides were then washed with wash buffer, (Dako S3006), then de ionized water and mounted with Dako Faramount, (S3025).

Results:

All ten chromogen produced visible dots. In the 1+ cell line, approx 2-3 dots were produced on slides 1, 2, 3, 4, 5, 7, 8 and 10. On slides 7 and 9, fewer and smaller dots were seen, indicating dots below visible detection limit. Below the dots and each chromogen is commented.
Slide 1: Bright red dots, up to 4 micron in diameter. There was virtually no background. Very easily seen even at 10× objective
Slide 2: Bright orange red dots, up to 4 micron in diameter. There was virtually no background. Very easily seen even at 10× objective. Further experiments showed very good contrast to blue haematoxilin.
Slide 3: Dark purple to black dots, up to 4 micron in diameter. Little background. Very easily seen even at 10× objective.
Slide 4: Black dots, up to 5 micron in diameter. Some grayish background. Very easily seen even at 10× objective.
Slide 5: Brown dots, up to 3 micron in diameter. Little background. Very easily seen even at 10× objective.
Slide 6: Very faint yellow dots below 1 micron in diameter. Viewing required either 20 or 40× objectives. Further control experiments showed that addition of 2% piperidine to the mounting media significantly increased visible dot size to 1-2 microns, and made the dots more brownish-yellow. Even without piperidine, the dots were extremely intense green when viewed in a fluorescence microscope.
Slide 7: Violet dots, up to 1 micron in diameter. Extremely intense red when viewed in a fluorescence microscope.
Slide 8: Dark blue dots, up to 4 micron in diameter. Slight blue background. Very easily seen even at 10× objective
Slide 9: Brownish dots, below 1 micron in diameter.
Slide 10: Brownish red dots, up to 2 micron in diameter.

Experiment 4. Visualization of Two Targets (a Biomarker Protein and a Reference Protein) in a Histological Sample Satined with Haematoxylin Slides with HER2 control cell lines were pretreated as in experiment 1, and subjected to the following staining protocol on the Autostainer:
Pre rinse with wash buffer (Dako S3006)
Peroxidase blocking solution (Dako S2023), 5 min.
Wash (Dako S3006)
antiHer2 antibody, clone Dak 3-25-11, 6 nM, and anti-Cytokeratine Dako M3515 6 nM for 10 min.
Wash (Dako S3006)
Goat-anti-Rabbit-Dextran70-HRP, (Lit 348.111, fraction 10-11) 4 pM in incubation media 1, 10 min.

5 microM Fer-(Lys(Fer))₃-L150-Lys(Flu) (Lit 370.073/D20171), 5 mM alphaCyano-Hydroxy Cinnamic acid with 0.6 mM hydrogen peroxide in incubation media 2, for 10 min.

Wash (Dako S3006)

antiFITC-F(ab)$_1$-(AP)$_1$, 20 nM and Goat-anti-Mouse-Dextran70-HRP, 25 nM in incubation media 1, 10 min Wash (Dako S3006)

Liquid Permanent Red, (Dako K0640), 10 min

Wash (Dako S3006)

DAB, (Dako K5007), varying time, 10, 8, 5, 3, 2, 1 min

Wash (Dako S3006)

Haematoxilin (Dako S3301)

Wash de-ionized water

Wash (Dako S3006)

The slides were mounted with Dako Faramount, (S3025).

Results:

The slides were double stained for Her2 (step (a)—red dots) and cytokeratin (step (b)—uniform brown DAB stain). The dots were counted and the expression levels of Her2 in the 1+ and 0+ cell lines were evaluated (in the 3+ cell line the staining generated too many dots, to be counted, so the level of expression of Her2 was not evaluated in this case). Approximately three times more dots were observed in the 1+ cell line compared to the 0+, which in concordance with the previous observations of the Her2 expression levels in these cells. 5 minutes deposition of DAB stain (step b) resulted in moderate homogeneous brown DAB stain of cytokeratin in cytoplasm of all three cell lines.

This experiment demonstrates a three color combination of a conventional IHC (brown), unconventional dotted IHC stain (red dots) and a histological stain (haematoxylin—blue) and, staining of two different targets with two different IHC stains.

The invention claimed is:

1. A method for visualization of a single target in a histological sample comprising a plurality of single target units, wherein the single target is a protein or a nucleic acid, the method comprising, in any order,
  (a) staining the histological sample with a first stain,
  (b) staining the histological sample with a second stain, and
  (c) staining the histological sample with a third stain,
wherein
(i) the first stain and the second stain are each generated via an enzyme-mediated deposition of a detectable enzyme substrate at sites of the histological sample comprising the single target units;
(ii) the first stain visualizes a first fraction of the total single target units, and the second stain visualizes a second fraction of the total single target units;
(iii) the first stain and second stain have different staining patterns, wherein the first stain staining pattern consists of distinct dots of the stain at sites of the histological sample comprising the single target units; and
(iv) the third stain is a histological stain that visualizes morphological features of the histological sample and does not visualize the identical single target units.

2. The method according to claim 1, wherein the first fraction of total single target units is a minor fraction of the total single target units in the histological sample, and the second fraction of total single target units is a major fraction of the total single target units in the sample.

3. The method according to claim 1, wherein the first stain differs from the second stain by optical features.

4. The method according to claim 1, wherein the distinct dots of the first stain have a diameter from around 0.4 micrometers to around 4 micrometers.

5. The method according to claim 1, wherein the third stain is hematoxylin.

6. The method according to claim 1, wherein the single target is a biological marker.

7. The method of claim 1, wherein each of the plurality of single target units comprise the same protein or nucleic acid molecule.

8. The method of claim 1, wherein the second fraction is 1% to 60% of the total single target units.

9. The method of claim 1, wherein the second stain staining pattern is a uniform staining pattern.

10. The method according to claim 1, wherein staining step (a) and staining step (b) each employ single target-specific binding agents to link the single target units to the enzyme.

11. The method according to claim 10, wherein the at least one specific binding agent of staining step (a) and the at least one specific binding agent of staining step (b) each comprise an antibody, nucleic acid, or nucleic acid analog.

12. The method according to claim 10, wherein the single target-specific binding agent of staining step (a) and the single target-specific binding agent of staining step (b) are members of specific binding pairs with the single target units.

13. The method according to claim 12, wherein the at least one single target-specific binding agent of staining step (a) and the at least one single target-specific binding agent of staining step (b) are the same binding molecule.

14. The method according to claim 12, wherein the at least one specific binding agent of staining step (a) and the at least one specific binding agent of staining step (b) are different binding molecules.

15. The method according to claim 1, wherein the first and the second stain are generated via deposition of a detectable enzyme substrate mediated by the same enzyme.

16. The method according to claim 15, wherein the enzyme is horseradish peroxidase.

17. The method according to claim 1, wherein the first stain is generated via deposition of the detectable enzyme substrate mediated by a first enzyme, and wherein the second stain is generated via deposition of the detectable substrate mediated by a second enzyme, wherein the first and second enzymes are different enzymes.

18. The method according to claim 17, wherein the enzyme generating the first stain is horseradish peroxidase and the enzyme generating the second stain is alkaline phosphatase.

19. The method according to claim 1, further comprising determining the amount of the single target in the sample.

20. The method according to claim 19, wherein the amount is the total amount of the single target in the sample.

21. A method for visualization of a single target in a histological sample comprising a plurality of single target units, wherein the single target is a protein or a nucleic acid, the method comprising, in any order,
  (a) staining the histological sample with a first stain,
  (b) staining the histological sample with a second stain, and
  (c) staining the histological sample with a third stain,
wherein
(i) the first stain and the second stain are each generated via an enzyme-mediated deposition of a detectable enzyme substrate at sites of the histological sample comprising the single target units;

(ii) the first stain visualizes a first fraction of the total single target units, and the second stain visualizes a second fraction of the total single target units;

(iii) the first stain and second stain have different staining patterns, wherein the first staining pattern comprises distinct dots of the stain at sites of the histological sample comprising the single target units; and (iv) the third stain is a histological stain that visualizes morphological features of the histological sample and does not visualize the single target units.

* * * * *